(12) United States Patent
Frazier et al.

(10) Patent No.: US 6,419,669 B1
(45) Date of Patent: Jul. 16, 2002

(54) METHOD AND APPARATUS FOR PATCHING A TISSUE OPENING

(75) Inventors: Andrew G. C. Frazier, Sunnyvale; Michael D. Lesh, Mill Valley; Chad C. Roue, Fremont; Erik J. van der Burg, Sunnyvale, all of CA (US)

(73) Assignee: Appriva Medical, Inc., Sunnyvale, CA (US)

( * ) Notice: Subject to any disclaimer, the term of this patent is extended or adjusted under 35 U.S.C. 154(b) by 0 days.

(21) Appl. No.: 09/447,390

(22) Filed: Nov. 22, 1999

Related U.S. Application Data

(63) Continuation-in-part of application No. 09/399,521, filed on Sep. 20, 1999, now Pat. No. 6,231,561.

(51) Int. Cl.[7] .............................................. A61M 31/00
(52) U.S. Cl. ...................................... 604/500; 604/107
(58) Field of Search ................................ 606/108, 198, 606/107, 500, 115, 117, 507, 511, 139

(56) References Cited

U.S. PATENT DOCUMENTS

| | | |
|---|---|---|
| 3,874,388 A | 4/1975 | King et al. |
| 4,007,743 A | 2/1977 | Blake |
| 4,710,192 A | 12/1987 | Liotta et al. |
| 4,950,285 A | 8/1990 | Wilk |
| 5,108,420 A | 4/1992 | Marks |
| 5,123,428 A | 6/1992 | Schwarz |
| 5,171,259 A | 12/1992 | Inoune |
| 5,281,238 A | 1/1994 | Chin et al. |
| 5,282,827 A | 2/1994 | Kensey et al. |
| 5,306,234 A | 4/1994 | Johnson |
| 5,350,399 A | 9/1994 | Erlebacher et al. |
| 5,373,840 A | 12/1994 | Knighton |
| 5,375,612 A | 12/1994 | Cottenceau et al. |
| 5,403,326 A | 4/1995 | Harrison et al. |
| 5,417,699 A | 5/1995 | Klein et al. |
| 5,527,338 A | 6/1996 | Purdy |
| 5,593,422 A | 1/1997 | Muijs Van Der Moer et al. |
| 5,593,424 A | 1/1997 | Northrup, III |
| 5,632,753 A | 5/1997 | Loeser |
| 5,709,224 A | 1/1998 | Behl et al. |
| 5,713,907 A | 2/1998 | Hogendijk et al. |
| 5,746,747 A | 5/1998 | McKeating |
| 5,814,068 A | 9/1998 | Koike et al. |
| 5,827,268 A | 10/1998 | Laufer |
| 5,860,991 A | 1/1999 | Klein et al. |
| 5,865,791 A | 2/1999 | Whayne et al. |
| 5,879,366 A | 3/1999 | Shaw et al. |
| 5,957,900 A | 9/1999 | Ouchi |
| 5,968,053 A | 10/1999 | Revelas |
| 6,280,414 B1 | 8/2000 | Shah et al. |
| 6,290,674 B1 | 9/2001 | Roue et al. |
| 6,328,727 B1 | 12/2001 | Frazier et al. |

OTHER PUBLICATIONS

Blackshear JL, Odel JA., *Appendage Obliteration to Reduce Stroke in Cardiac Surgical Patients With Atrial Fibrillation*. Ann Thorac. Surg., 1996.61(2): 755–9.

Lindsay BD., *Obliteration of the Left Atrial Appendage: A Concept Worth Testing*, Ann Thorac. Surg., 1996.61(2): 515.

*Primary Examiner*—Manuel Mendez
(74) *Attorney, Agent, or Firm*—Knobbe, Martens, Olson & Bear, LLP

(57) ABSTRACT

Disclosed is a closure catheter, for patching a tissue opening such as an atrial septal defect, patent foreman ovale, or the left atrial appendage of the heart. The closure catheter carries a deployable patch and a plurality of tissue anchors, which may be deployed to secure the patch to surrounding tissue. Methods are also disclosed.

24 Claims, 16 Drawing Sheets

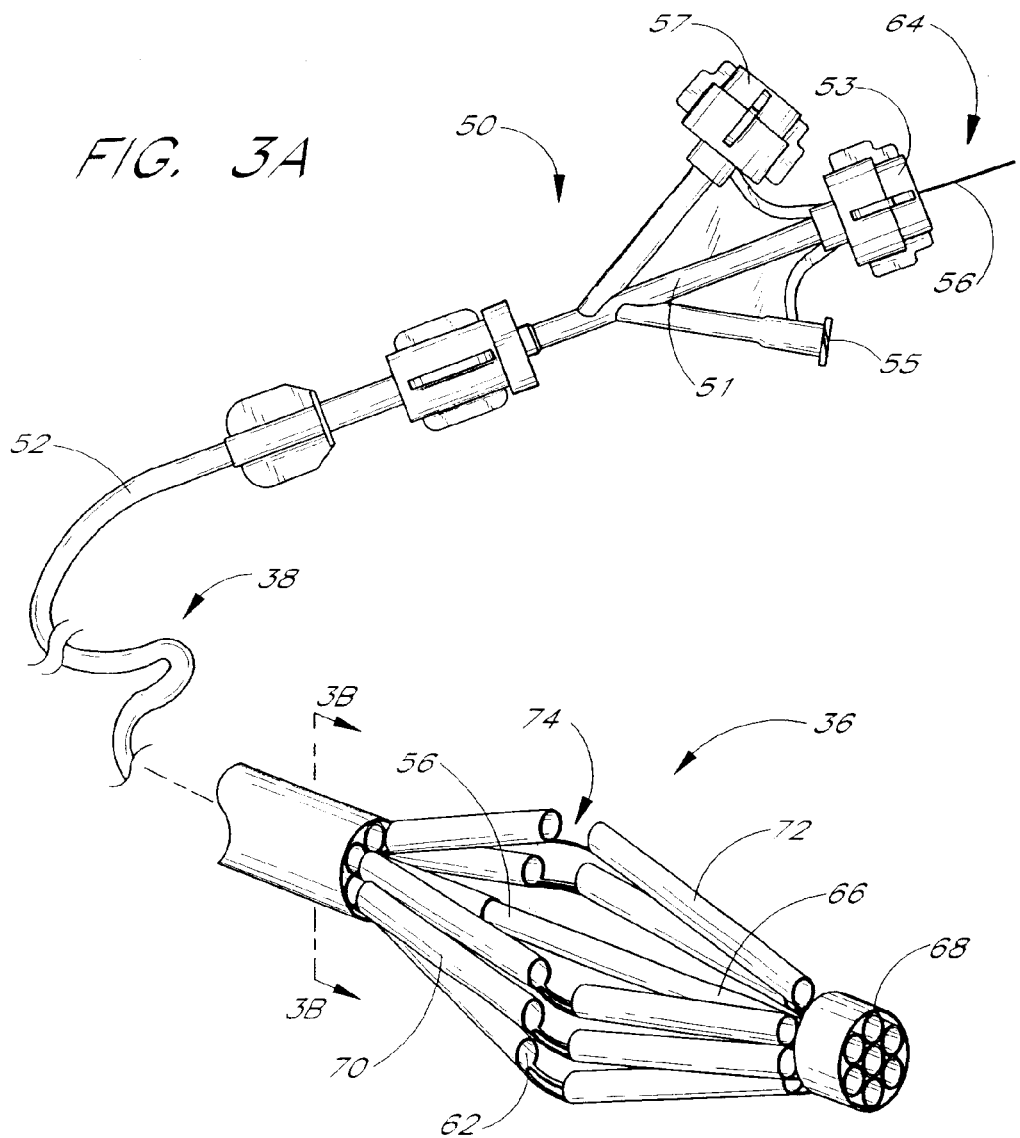
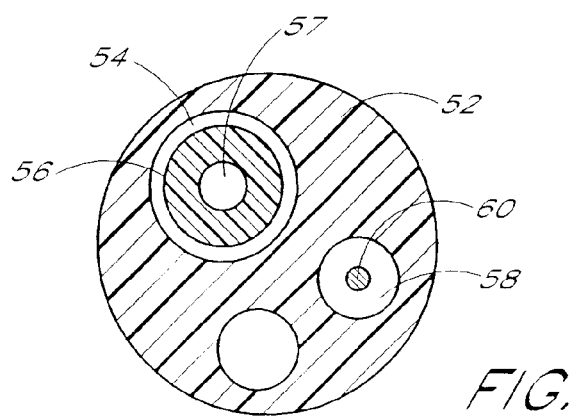

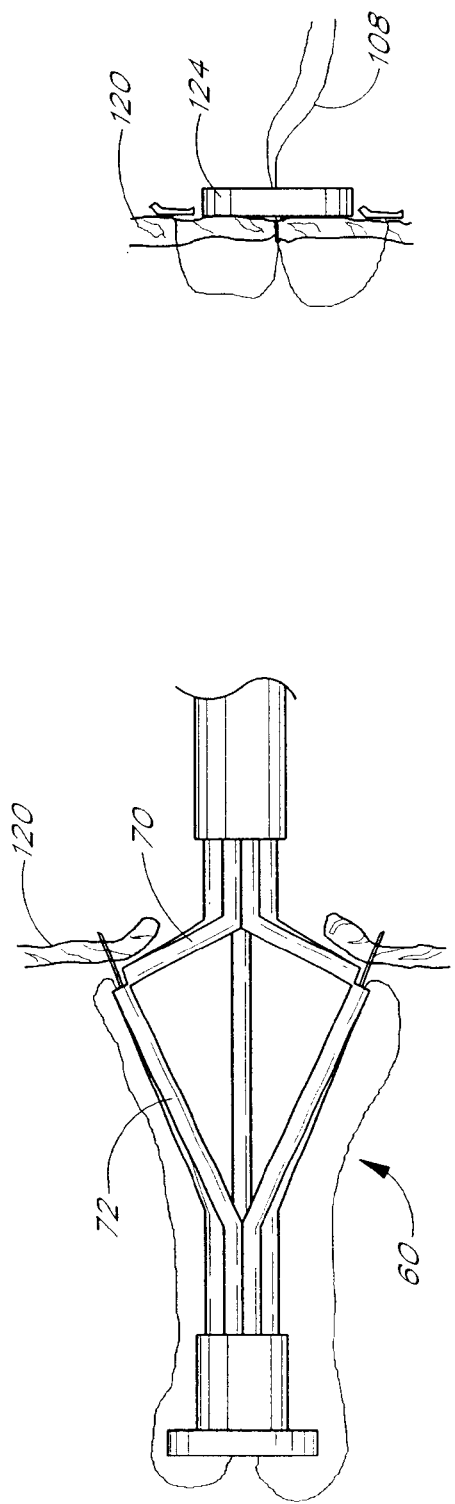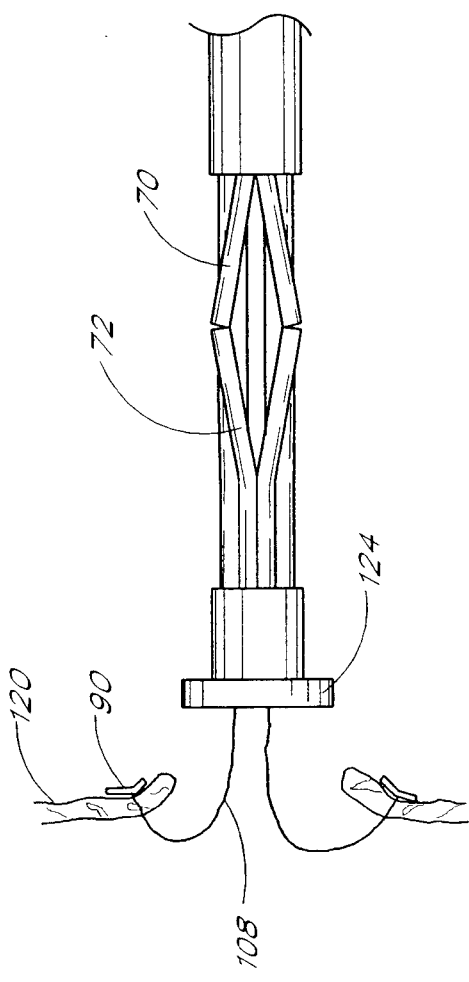
FIG. 13
FIG. 14
FIG. 15

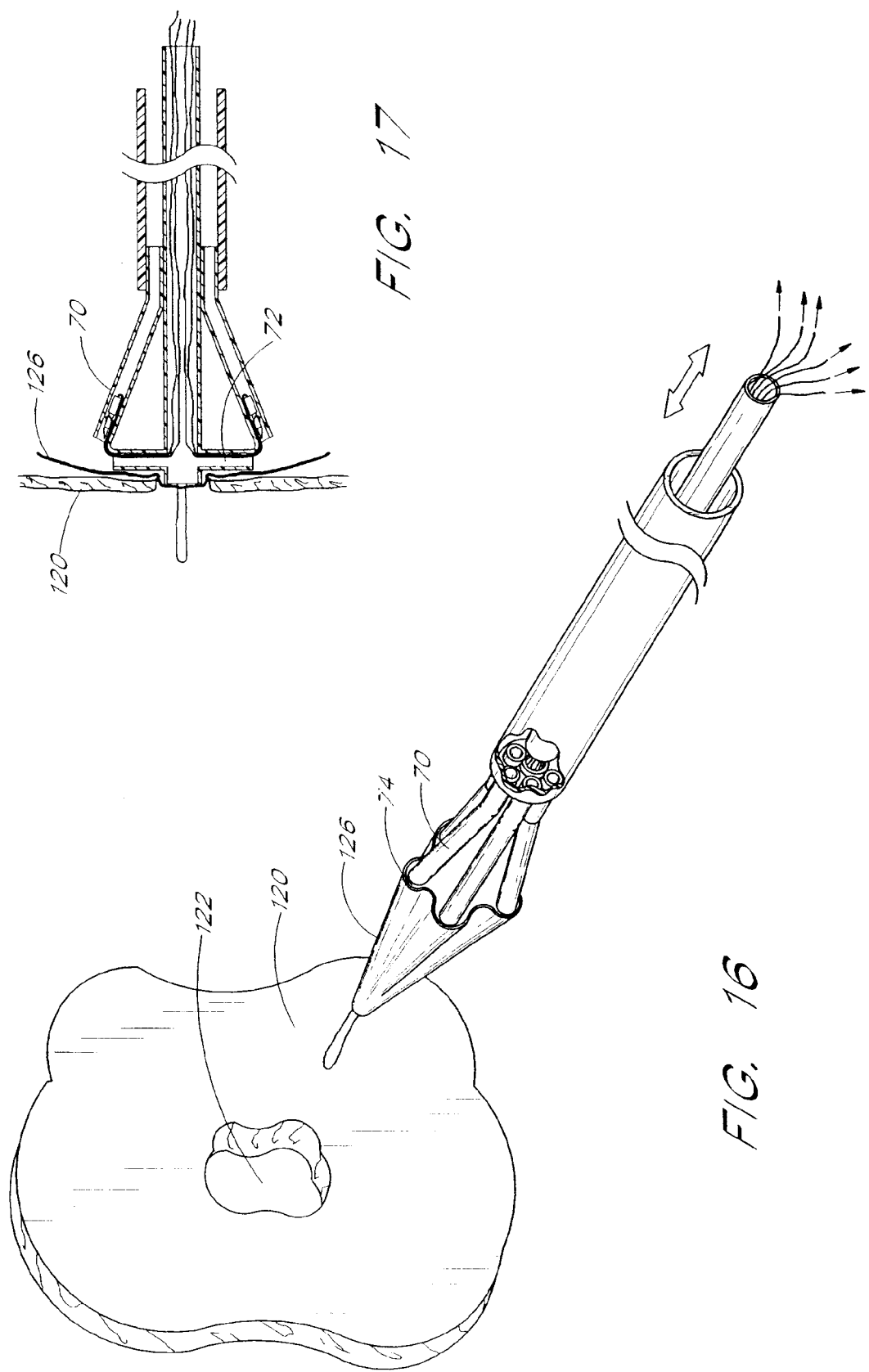

METHOD AND APPARATUS FOR PATCHING A TISSUE OPENING

This application is a continuation-in-part of application Ser. No. 09/399,521, filed Sep. 20, 1999, and now U.S. Pat. No. 6,231,561.

The present invention relates to methods and devices for closing a body lumen, tissue opening, or cavity and, in particular, for closing an atrial septal defect.

BACKGROUND OF THE INVENTION

Embolic stroke is the nation's third leading killer for adults, and is a major cause of disability. There are over 700,000 strokes per year in the United States alone. Of these, roughly 100,000 are hemoragic, and 600,000 are ischemic (either due to vessel narrowing or to embolism). The most common cause of embolic stroke emanating from the heart is thrombus formation due to atrial fibrillation. Approximately 80,000 strokes per year are attributable to atrial fibrillation. Atrial fibrillation is an arrhythmia of the heart that results in a rapid and chaotic heartbeat that produces lower cardiac output and irregular and turbulent blood flow in the vascular system. There are over five million people worldwide with atrial fibrillation, with about four hundred thousand new cases reported each year. Atrial fibrillation is associated with a 500 percent greater risk of stroke due to the condition. A patient with atrial fibrillation typically has a significantly decreased quality of life due, in part, to the fear of a stroke, and the pharmaceutical regimen necessary to reduce that risk.

For patients who develop atrial thrombus from atrial fibrillation, the clot normally occurs in the left atrial appendage (LAA) of the heart. The LAA is a cavity which looks like a small finger or windsock and which is connected to the lateral wall of the left atrium between the mitral valve and the root of the left pulmonary vein. The LAA normally contracts with the rest of the left atrium during a normal heart cycle, thus keeping blood from becoming stagnant therein, but often fails to contract with any vigor in patients experiencing atrial fibrillation due to the discoordinate electrical signals associated with AF. As a result, thrombus formation is predisposed to form in the stagnant blood within the LAA.

Blackshear and Odell have reported that of the 1288 patients with non-rheumatic trial fibrillation involved in their study, 221 (17%) had thrombus detected in the left atrium of the heart. Blackshear J L, Odell J A., Appendage Obliteration to Reduce Stroke in Cardiac Surgical Patients With Atrial Fibrillation. Ann Thorac. Surg., 1996.61(2):755–9. Of the patients with atrial thrombus, 201 (91%) had the atrial thrombus located within the left atrial appendage. The foregoing suggests that the elimination or containment of thrombus formed within the LAA of patients with atrial fibrillation would significantly reduce the incidence of stroke in those patients.

Pharmacological therapies for stroke prevention such as oral or systemic administration of warfarin or the like have been inadequate due to serious side effects of the medications and lack of patient compliance in taking the medication. Invasive surgical or thorascopic techniques have been used to obliterate the LAA, however, many patients are not suitable candidates for such surgical procedures due to a compromised condition or having previously undergone cardiac surgery. In addition, the perceived risks of even a thorascopic surgical procedure often outweigh the potential benefits. See Blackshear and Odell, above. See also Lindsay B D., Obliteration of the Left Atrial Appendage: A Concept Worth Testing, Ann Thorac. Surg., 1996.61(2):515.

Despite the various efforts in the prior art, there remains a need for a minimally invasive method and associated devices for reducing the risk of thrombus formation in the left atrial appendage.

Other conditions which would benefit from a tissue aperture closure catheter are tissue openings such as an atrial septal defect. In general, the heart is divided into four chambers, the two upper being the left and right atria and the two lower being the left and right ventricles. The atria are separated from each other by a muscular wall, the interatrial septum, and the ventricles by the interventricular septum.

Either congenitally or by acquisition, abnormal openings, holes or shunts can occur between the chambers of the heart or the great vessels (interatrial and interventricular septal defects or patent ductus arteriosus and aorthico-pulmonary window respectively), causing shunting of blood through the opening. The ductus arteriosus is the prenatal canal between the pulmonary artery and the aortic arch which normally closes soon after birth. The deformity is usually congenital, resulting from a failure of completion of the formation of the septum, or wall, between the two sides during fetal life when the heart forms from a folded tube into a four-chambered, two unit system.

These deformities can carry significant sequelae. For example, with an atrial septal defect, blood is shunted from the left atrium of the heart to the right, producing an over-load of the right heart. In addition to left-to-right shunts such as occur in patent ductus arteriosus from the aorta to the pulmonary artery, the left side of the heart has to work harder because some of the blood which it pumps will recirculate through the lungs instead of going out to the rest of the body. The ill effects of these lesions usually cause added strain on the heart with ultimate failure if not corrected.

Previous extracardiac (outside the heart) or intracardiac septal defects have required relatively extensive surgical techniques for correction. To date the most common method of closing intracardiac shunts, such as atrial-septal defects and ventricular-septal defects, entails the relatively drastic technique of open-heart surgery, requiring opening the chest or sternum and diverting the blood from the heart with the use of a cardiopulmonary bypass. The heart is then opened, the defect is sewn shut by direct suturing with or without a patch of synthetic material (usually of Dacron, Teflon, silk, nylon or pericardium), and then the heart is closed. The patient is then taken off the cardiopulmonary bypass machine, and then the chest is closed.

In place of direct suturing, closures of interauricular septal defects by means of a mechanical prosthesis have been disclosed.

U.S. Pat. No. 3,874,388 to King, et al. relates to a shunt defect closure system including a pair of opposed umbrella-like elements locked together in a face to face relationship and delivered by means of a catheter, whereby a defect is closed. U.S. Pat. No. 5,350,399 to Erlebacher, et al. relates to a percutaneous arterial puncture seal device also including a pair of opposed umbrella-like elements and an insertion tool.

U.S. Pat. No. 4,710,192 to Liotta, et al. relates to a vaulted diaphragm for occlusion in a descending thoracic aorta.

U.S. Pat. No. 5,108,420 to Marks relates to an aperture occlusion device consisting of a wire having an elongated configuration for delivery to the aperture, and a preprogrammed configuration including occlusion forming wire segments on each side of the aperture.

U.S. Pat. No. 4,007,743 to Blake relates to an opening mechanism for umbrella-like intravascular shunt defect closure device having foldable flat ring sections which extend between pivotable struts when the device is expanded and fold between the struts when the device is collapsed.

Notwithstanding the foregoing, there remains a need for a transluminal method and apparatus for correcting intracardiac septal defects, which enables a patch to placed across a septal defect to inhibit or prevent the flow of blood therethrough.

SUMMARY OF THE INVENTION

The present invention provides a closure catheter and methods for closing an opening in tissue, a body lumen, hollow organ or other body cavity. The catheter and methods of its use are useful in a variety of procedures, such as treating (closing) wounds and naturally or surgically created apertures or passageways. Applications include, but are not limited to, atrial septal defect closure, patent ductus arteriosis closure, aneurysm isolation and graft and/or bypass anastomosis procedures.

There is provided in accordance with one aspect of the present invention, a method of patching an intracardiac septal defect such as an atrial septal defect. The method comprises the steps of providing a catheter having an elongate flexible body with a proximal end and a distal end, a patch and at least two anchors removably carried by the distal end. The distal end is advanced to a position near the atrial septal defect, and the patch is positioned across the defect. The anchors are thereafter deployed from the catheter to secure the patch across the defect.

In one embodiment, the positioning step comprises enlarging the cross section of the patch from a reduced profile for advancing the catheter, to an enlarged profile for patching the defect. The positioning step comprises inclining at least one patch support from an axial orientation to an inclined orientation to position the patch across the defect. The positioning step preferably comprises inclining at least three patch supports from an axial orientation to an inclined orientation to position the patch across the defect. In one embodiment, the deploying the anchors step comprises advancing the anchors distally through the patch and into tissue adjacent the defect to secure the patch across the defect.

In accordance with another aspect of the present invention, there is provided a method of closing an opening in a subcutaneous tissue plane. The method comprises the steps of providing a catheter having a patch and at least one anchor. The catheter is advanced to the opening, and the patch is positioned across the opening. The anchor is advanced into tissue to secure the patch across the opening. Preferably, the advancing the anchor step comprises advancing at least three anchors into the tissue to secure the patch across the opening. The opening may be a naturally occurring opening such as an atrial septal defect, or a surgically created opening.

In accordance with a further aspect of the present invention, there is provided a deployment catheter for deploying a patch across a tissue aperture. The deployment catheter comprises an elongate body having a proximal end and a distal end. At least one patch support is provided on the body for removably carrying a patch. At least one anchor support is also provided for removably carrying at least one anchor. The anchor support is movable between an axial orientation and an inclined orientation with respect to a longitudinal axis of the body. In one embodiment, the anchor support is hingably connected to the patch support. The anchor support and patch support may also be the same structure, such that the patch is carried by the anchor supports. Preferably, at least three anchor supports and/or at least three patch supports are provided.

In accordance with a further aspect of the present invention, there is provided a patch deployment catheter for deploying a patch across an opening. The catheter comprises an elongate body, having a proximal end and a distal end. At least two supports are provided on the catheter, movable between an axial orientation and an inclined orientation. Each support comprises a proximal section, a distal section and a hinge in-between. A control is provided on the catheter for moving the hinge radially outwardly from a first position for introducing the catheter to a site in the body to a second position for deploying the patch at the site. The supports are in the axial orientation when the hinge is in the first position.

In one embodiment, the elongate body is flexible. Preferably, at least one tissue anchor is carried by the proximal section of each support. At least one patch is preferably carried by the distal section of each support. In one embodiment, the patch comprises a tissue ingrowth surface.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 3A is an enlarged perspective view of the distal end of a closure catheter in accordance with the present invention.

FIG. 3B is a cross section taken along the lines 3B—3B of FIG. 3A.

FIG. 13 is a side elevational partial cross-section of the catheter of FIG. 12, in an anchor deployment orientation within the aperture.

FIG. 14 is a side elevational partial cross-section as in FIG. 13, with the deployment catheter withdrawn from the aperture.

FIG. 15 is a side elevational cross section through the aperture, which has been closed in accordance with the present invention.

FIG. 16 is a perspective view of a closure catheter in accordance with the present invention, carrying an aperture patch.

FIG. 17 is a cross-sectional view through the catheter of FIG. 16, shown deploying a patch across a tissue aperture.

DETAILED DESCRIPTION OF THE PREFERRED EMBODIMENT

For simplicity, the present invention will be described primarily in the context of a left atrial appendage closure procedure. However, the device and methods herein are readily applicable to a wider variety of closure or attachment procedures, and all such applications are contemplated by the present inventors. For example, additional heart muscle procedures such as atrial septal defect closure and patent ductus arteriosis closure are contemplated. Vascular procedures such as isolation or repair of aneurysms, anastomosis of vessel to vessel or vessel to prosthetic tubular graft (e.g., PTFE or Dacron tubes, with or without wire support structures as are well known in the art) joints may also be accomplished using the devices of the present invention. Attachment of implantable prostheses, such as attachment of the annulus of a prosthetic tissue or mechanical heart valve may be accomplished. A variety of other tissue openings, lumens, hollow organs and surgically created passageways may be closed, patched or reduced in volume in accordance with the present invention. For example, an opening in a tissue plane may be closed or patched, such as by attaching a fabric or tissue sheet across the opening. In one specific application, the device of the present invention is used to anchor a fabric patch to close an atrial septal defect. The target aperture or cavity may be accessed transluminally (e.g., vascular catheter or endoscope) or through solid tissue, such as transmural, percutaneous or other approach. The present invention may also be used in an open surgical procedure such as to close the left atrial appendage during open heart surgery to correct or address a different condition. In another example, the device is advanced through the percutaneous opening and used to close a vascular puncture such as a femoral artery access site for a PTA or other diagnostic or therapeutic interventional procedure. Adaptation of the devices and methods disclosed herein to accomplish procedures such as the foregoing will be apparent to those of skill in the art in view of the disclosure herein.

Figure 1:
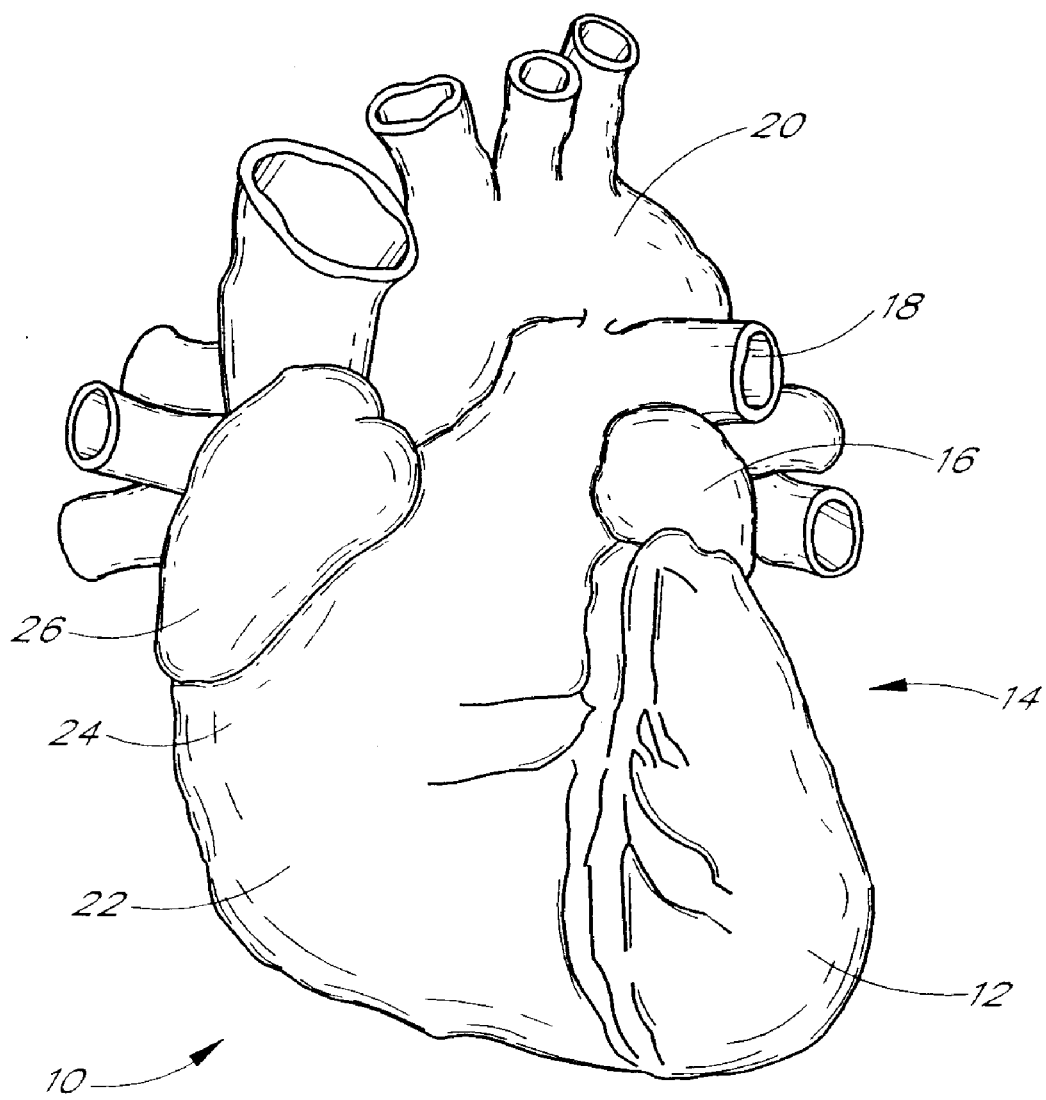
FIG. 1 is an anterior illustration of a heart, with the proximal parts of the great vessels.

Referring to FIG. 1, a heart 10 is illustrated to show certain portions including the left ventricle 12, the left atrium 14, the left atrial appendage (LAA) 16, the pulmonary artery 18, the aorta 20, the right ventricle 22, the right atria 24, and the right atrial appendage 26. As is understood in the art, the left atrium 14 is located above the left ventricle 12 and the two are separated by the mitral valve (not illustrated). The LAA 16 is normally in fluid communication with the left atrium 14 such that blood flows in and out of the LAA 16 as the heart 10 beats.

In accordance with the present invention, a closure catheter 38 is advanced through the heart and into the LAA. In general, the closure catheter 38 is adapted to grasp tissue surrounding the opening to the LAA, and retract it radially inwardly to reduce the volume of and/or close the LAA. The LAA is thereafter secured in its closed orientation, and the closure catheter 38 is removed. Specific aspects of one embodiment of the closure catheter in accordance with the present invention are described in greater detail below.

The LAA may be accessed through any of a variety of pathways as will be apparent to those of skill in the art. Transeptal access, as contemplated by FIG. 2, may be achieved by introducing a transeptal catheter through the femoral or jugular vein, and transluminally advancing the catheter into the right atrium. Once in the right atrium, a long hollow needle with a preformed curve and a sharpened distal tip is forcibly inserted through the fossa ovalis. A radiopaque contrast media may then be injected through the needle to allow visualization and ensure placement of the needle in the left atrium, as opposed to being in the pericardial space, aorta, or other undesired location.

Once the position of the needle in the left atrium is confirmed, the transeptal catheter is advanced into the left atrium. The closure catheter 38 may then be advanced through the transeptal catheter 30, and steered or directed into the left atrial appendage. Alternative approaches include venous transatrial approaches such as transvascular advancement through the aorta and the mitral valve. In addition, the devices of the present invention can be readily adapted for use in an open heart surgical procedure, although transluminal access is presently preferred.

Figure 2:
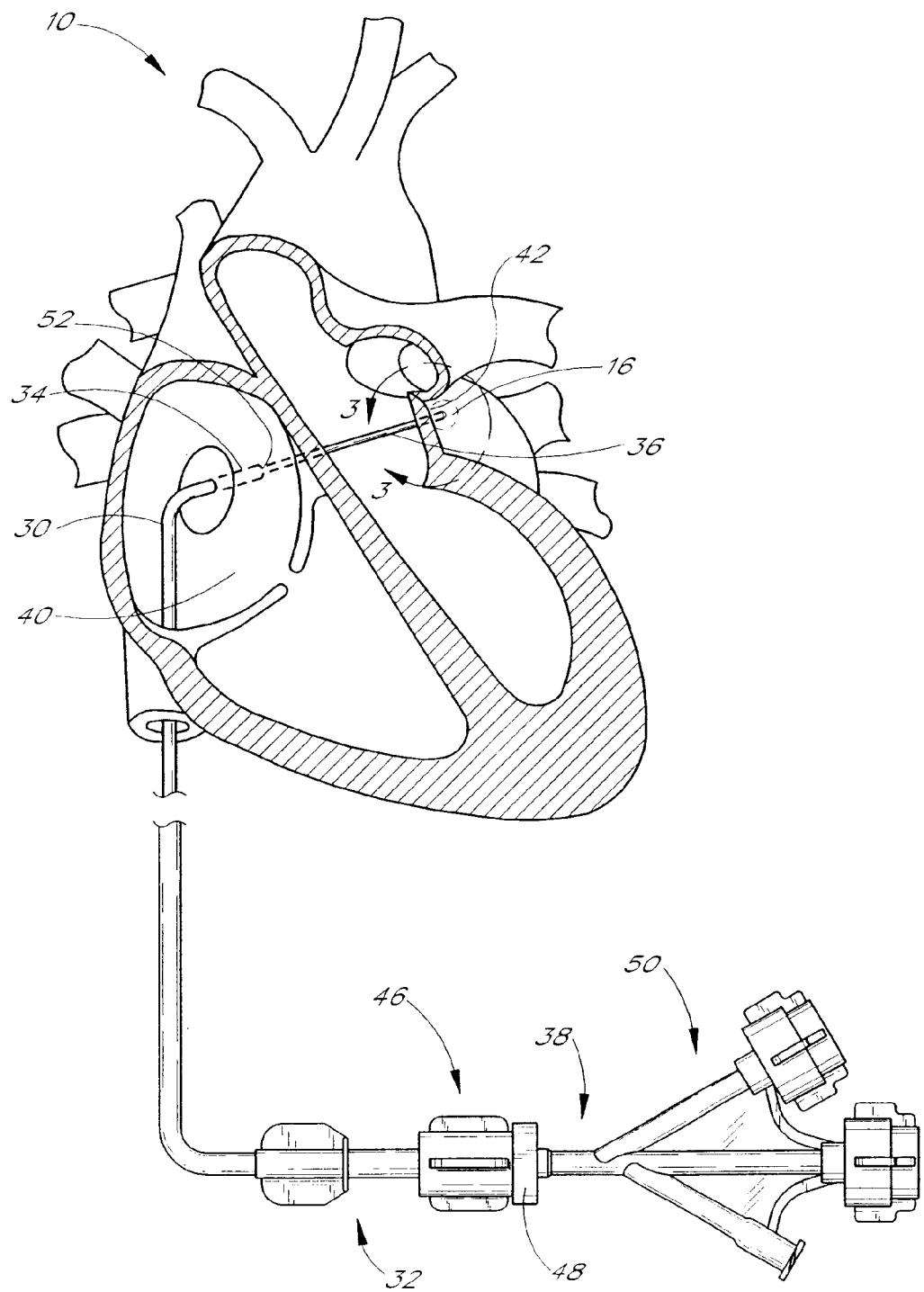
FIG. 2 is a schematic cross section through the heart with a transeptal catheter deployed through the septum and a closure catheter extending into the LAA.

Thus, referring to FIG. 2, a transeptal catheter 30 has a proximal end 32 and a distal end 34. The distal end 34 of the transeptal catheter 30 has breached the septum 40 of the patient's heart 10 and is disposed adjacent the opening 42 of the patient's LAA 16. The distal end 36 of a closure catheter 38 extends from the distal end 34 of the transeptal catheter 30 and into the LAA 16.

At the proximal end 46 of the transeptal catheter 30, a luer connector coupled to a hemostasis valve 48 prevents the egress of blood from a central lumen of the transeptal catheter 30. The proximal end 50 of the closure catheter 38 extends proximally from the hemostasis valve 48. Additional details concerning the use and design of transeptal access catheters are well known in the art and will not be discussed further herein.

Referring to FIGS. 2 and 3, the closure catheter 38 thus has a proximal end 50, a distal end 36, and an elongate flexible tubular body 52 extending therebetween. The axial length of the closure catheter 38 can be varied, depending upon the intended access point and pathway. For a femoral vein-transeptal approach, the closure catheter 38 generally has an axial length within the range of from about 100 cm to about 140 cm, and, in one embodiment, about 117 cm.

The outside diameter of the flexible body 52 can also be varied, depending upon the number of internal lumen and other functionalities as will be understood by those of skill in the art. In one embodiment, the outside diameter is about 12 FR (0.156 inches), and closure catheters are contemplated to have OD's generally within the range of from about 0.078 inches to about 0.250 inches. Diameters outside of the above range may also be used, provided that the functional consequences of the diameter are acceptable for the intended application of the catheter.

For example, the lower limit of the outside diameter for tubular body 52 in a given application will be a function of the number of fluid or other functional lumen contained within the catheter. In addition, tubular body 52 must have sufficient pushability to permit the catheter to be advanced to its target location within the heart without buckling or undesirable bending. The ability of the tubular body 52 to transmit torque may also be desirable, such as in embodiments in which the tissue anchor deployment guides are not uniformly circumferentially distributed about the distal end 36 of the catheter. Optimization of the outside diameter of the catheter, taking into account the flexibility, pushability and torque transmission characteristics can be accomplished through routine experimentation using conventional catheter design techniques well known to those of skill in the art.

The flexible body 52 can be manufactured in accordance with any of a variety of known techniques. In one embodiment, the flexible body 52 is extruded from any of a variety of materials such as HDPE, PEBAX, nylon, polyimide, and PEEK. Alternatively, at least a portion or all of the length of tubular body 52 may comprise a spring coil, solid walled hypodermic needle or other metal tubing, or braided reinforced wall, as are known in the art.

The proximal end 50 of the closure catheter 38 is provided with a manifold 51, having a plurality of access ports. Generally, manifold 51 is provided with an access port 53 which may be used as a guidewire port in an over the wire embodiment, and a deployment wire port 57. Additional access ports such as a contrast media introduction port 55, or others may be provided as needed, depending upon the functional requirements of the catheter.

The tubular body 52 has at least a first actuator lumen 54, for axially movably receiving an actuator 56. Actuator 56 extends between a proximal end 64 at about the proximal end of the closure catheter, and a distal end 66 at or near the distal end 36 of the closure catheter 38. The distal end 66 of the actuator 56 is secured to a cap 68. In the illustrated embodiment, the actuator lumen 54 is in communication with the access port 53 to permit the actuator 56 to extend proximally therethrough.

Actuator 56 can have a variety of forms, depending upon the construction of the anchor supports 62 on the distal end 36 of the closure catheter 38. In general, the catheter in the area of the anchor supports 62 should have a crossing profile of no more than about 14 French for transluminal advancement and positioning. However, the anchor supports must then be capable of directing tissue anchors into the wall of the cavity or lumen which may have an inside diameter on the order of about 1.5 cm to about 3 cm in the case of the LAA in an average adult. The device of the present invention can be readily scaled up or down depending upon the intended use, such as to accommodate a 5 cm to 10 cm cavity in GI tract applications or 5 mm to about 2 cm for vascular applications. For this purpose, the anchor supports are preferably moveable between a reduced cross sectional orientation and an enlarged cross sectional orientation to aim at, and, in some embodiments, contact the target tissue surface.

One convenient construction to accomplish the foregoing is for each anchor support 62 to take the form of a lever arm structure which is pivotably connected at one end to the catheter body. This construction permits inclination of the anchor support throughout a continuous range of outside diameters which may be desirable to aim the anchor and accommodate different treatment sites and/or normal anatomical variation within the patient population.

A laterally moveable anchor support can be moved between an axial orientation and an inclined orientation in a variety of ways. One convenient way is through the use of a pull wire or other actuator which increases the diameter of the deployment zone of the catheter in response to an axial shortening of fixed length moveable segments as disclosed in more detail below. For this construction, the actuator will be under pulling tension during actuation. Any of a variety of structures such as polymeric or metal single or multiple strand wires, ribbons or tubes can be used. In the illustrated embodiment, the actuator 56 comprises stainless steel tube, having an outside diameter of about 0.025 inches.

A pull wire can alternatively be connected to the radially outwardly facing surface and preferably near the distal end of each anchor support, and each anchor support is hingably attached at its proximal end to the catheter. Proximal traction on the pull wire will cause the anchor support to incline radially outwardly in the distal direction, and toward the target tissue.

In an alternate construction, the anchor support is inclined under a compressive force on the actuator 56. For example, the embodiment described in detail below can readily be converted to a push actuated system by axially immovable fixing the distal end of the anchor guide assembly to the catheter and slideably pushing the proximal end of the anchor guide assembly in the distal direction to achieve axial compression as will become apparent from the discussion below.

Push wire actuators have different requirements, than pull actuator systems, such as the ability to propagate a sufficient compressive force without excessive compression bending or friction. Thus, solid core wires or tubular structures may be preferred, as well as larger outside diameters compared to the minimum requirements in a pull actuated system. Thus, the inside diameter of the actuator lumen 57 may be varied, depending upon the actuator system design. In the illustrated embodiment, the actuator lumen 57 has an ID of about 0.038 inches, to slideably accommodate the 0.025 inch OD actuator 56.

A radially outwardly directed force on the anchor supports 62 can be provided by any of a variety of alternative expansion structures, depending upon desired performance and construction issues. For example, an inflatable balloon can be positioned radially inwardly from a plurality of hingably mounted anchor supports 62, and placed in communication with actuator lumen 54 which may be used as an inflation lumen. Any of a variety of balloon materials may be used, ranging in physical properties from latex for a highly compliant, low pressure system to PET for a non-compliant high pressure and consequently high radial force system, as is understood in the balloon angioplasty arts.

The tubular body 52 may additionally be provided with a guidewire lumen 57, or a guidewire lumen 57 may extend coaxially throughout the length of a tubular actuator 56 as in the illustrated embodiment.

The tubular body 52 may additionally be provided with a deployment lumen 58, for axially movably receiving one or more deployment elements 60 such as a wire, or suture for deploying one or more tissue anchors 90 into the target tissue 110. Deployment force for deploying the tissue anchors 90 can be designed to be in either the distal or proximal direction, and many of the considerations discussed above in connection with the actuator 56 and corresponding actuator lumen 54 apply to the deployment system as well. In the illustrated embodiment, deployment of the tissue anchors 90 is accomplished by proximal retraction on the deployment element 60 which, in turn, retracts deployment wire 106. Pushability is thus not an issue, and common suture such as 0.008 inch diameter nylon line may be used. For this embodiment, deployment lumen 58 has an inside diameter of about 0.038 inches. The deployment lumen 58 can be sized to receive either a single deployment element 60, or a plurality of deployment elements 106 such as a unique suture for each tissue anchor.

The distal end 36 of the closure catheter 38 is provided with one or more anchor supports 62, for removably carrying one or more tissue anchors. Preferably, two or more anchor supports 62 are provided, and, generally, in a device intended for LAA closure, from about 3 to about 12 anchor supports 62 are provided. In the illustrated embodiment, six anchor supports 62 are evenly circumferentially spaced around the longitudinal axis of the closure catheter 38.

Each anchor support 62 comprises a surface 63 for slideably retaining at least one tissue anchor, and permitting the tissue anchor to be aimed by manipulation of a control on the proximal end 50 of the closure catheter 38. Specific details of one embodiment of the anchor support 62 having a single anchor therein will be discussed below. Multiple anchors, such as two or three or more, can also be carried by each anchor support for sequential deployment.

The anchor supports 62 are movable between an axial orientation and an inclined orientation, in response to manipulation of a proximal control. The proximal control can take any of a variety of forms, such as slider switches or levers, rotatable levers or knobs, or the like, depending upon the desired performance. For example, a rotatable knob control can permit precise control over the degree of inclination of the anchor supports 62. A direct axial slider control, such as a knob or other grip directly mounted to the actuator 56 will optimize tactile feedback of events such as the anchor supports 62 coming into contact with the target tissue.

Each of the illustrated anchor supports 62 comprises at least a proximal section 70, a distal section 72, and a flex point 74. See FIG. 4. The distal end 73 of each distal section 72 is movably connected to the catheter body or the cap 68. In this embodiment, proximal retraction of the actuator 56 shortens the axial distance between the proximal end 71 of the proximal section 70 and the distal end 73 of distal section 72, forcing the flex point 74 radially outwardly from the longitudinal axis of the closure catheter 38. In this manner, proximal retraction of the actuator 56 through a controlled axial distance will cause a predictable and controlled increase in the angle between the proximal and distal sections 70 and 72 of the anchor support 62 and the longitudinal axis of the catheter. This is ideally suited for aiming a plurality of tissue anchors at the interior wall of a tubular structure, such as a vessel or the left atrial appendage.

Figure 4:
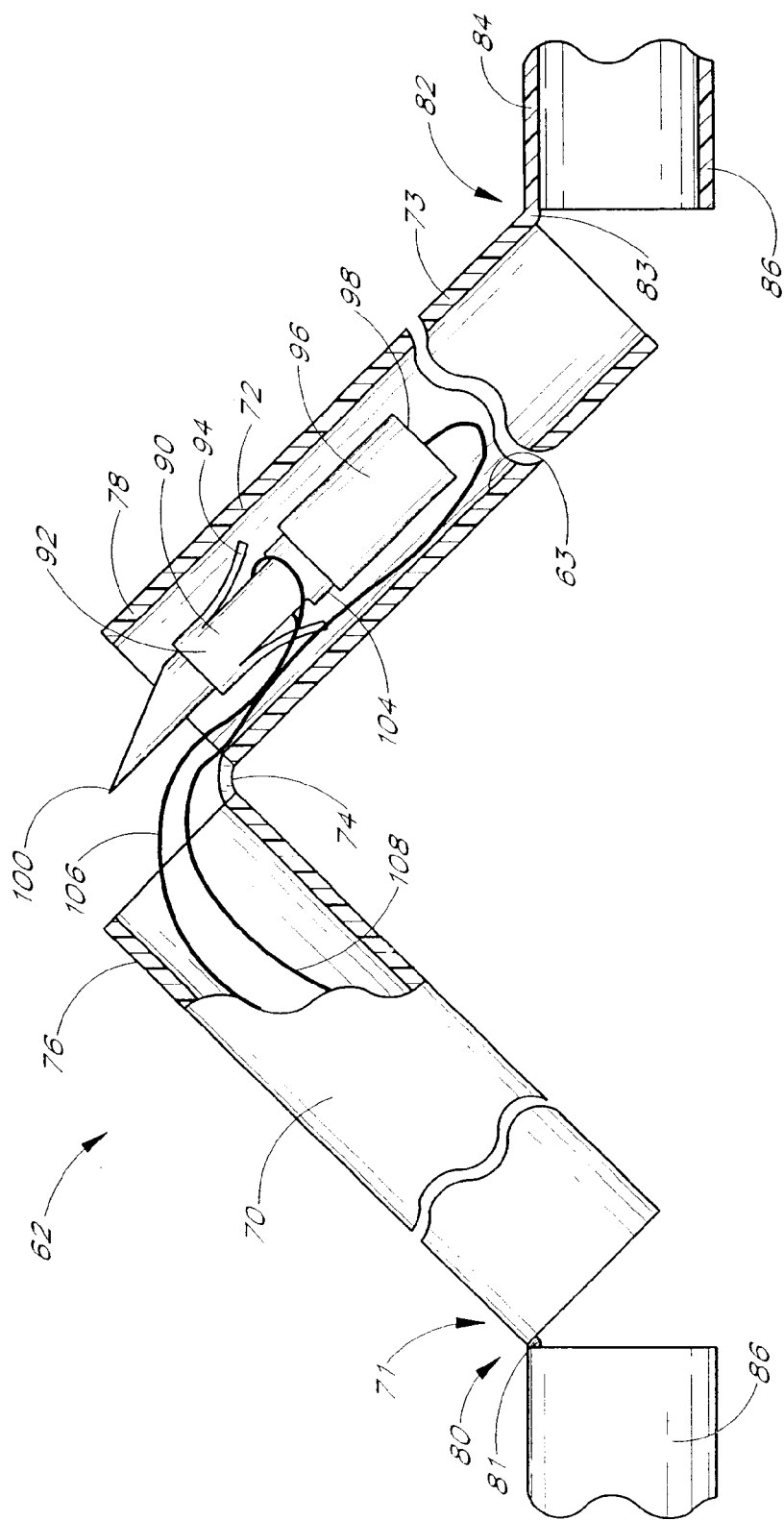
FIG. 4 is a partial cross-sectional view of a tissue anchor and introducer, positioned within an anchor guide in accordance with the present invention.
Figure 5:
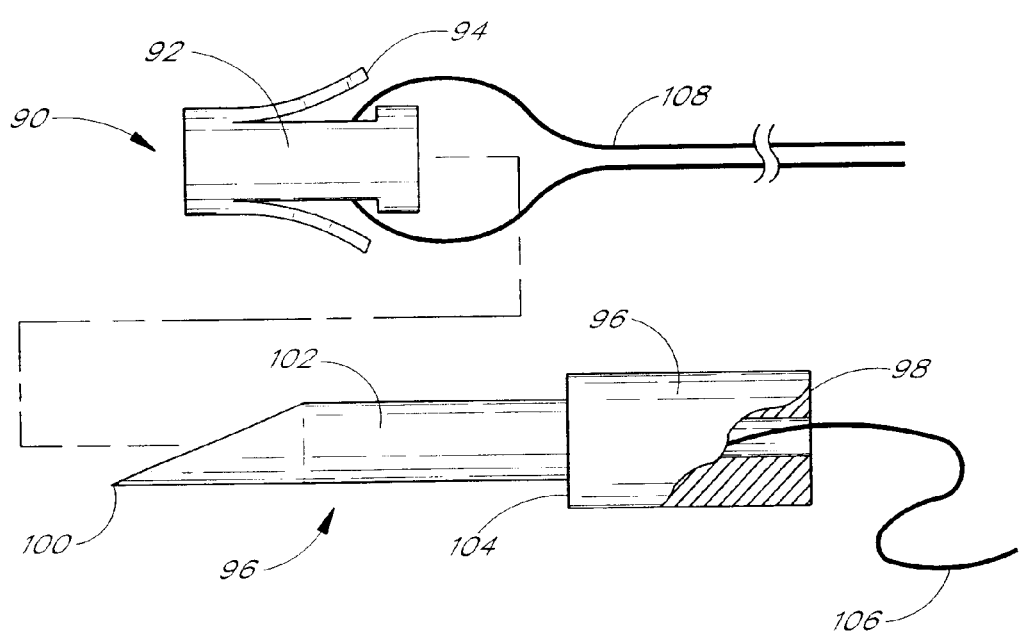
FIG. 5 is an exploded view of a tissue anchor and introducer in accordance with one aspect of the invention.

Referring to FIG. 4, there is illustrated an enlarged detailed view of one anchor support 62 in accordance with the present invention. The proximal section 70 and distal section 72 preferably comprise a tubular wall 76 and 78 joined at the flex point 74. In one embodiment, the proximal section 70 and distal section 72 may be formed from a single length of tubing, such as by laser cutting, photolithography, or grinding to separate the proximal section 70 from the distal section 72 while leaving one or two or more integrally formed hinges at flex point 74. Any of a variety of polymeric or metal tubing may be utilized for this purpose, including stainless steel, Nitinol or other super-elastic alloys, polyimide, or others which will be appreciated by those of skill in the art in view of the disclosure herein.

In the illustrated six tube embodiment, the proximal section 70 and distal section 72 are formed from a length of PEEK tubing having an inside diameter of about 0.038 inches, an outside diameter of about 0.045 inches and an overall length of about 1.4 inches. In general, if more than six anchor supports 62 are used, the diameter of each will be commensurately less than in the six tube embodiment for any particular application. When the proximal section 70 and the distal section 72 are coaxially aligned, a gap having an axial length of about 0.030 is provided therebetween. In the illustrated embodiment, the proximal section 70 and distal section 72 are approximately equal in length although dissimilar lengths may be desirable in certain embodiments. The length of the portion of the anchor support 62 which carries the tissue anchor 90 is preferably selected for a particular procedure or anatomy so that the anchor support 62 will be inclined at an acceptable launch angle when the deployment end of the anchor support 62 is brought into contact with the target tissue 110. Lengths from the hinge to the deployment end of the anchor support 62 within the range of from about 0.5 cm to about 1.5 cm are contemplated for the LAA application disclosed herein.

For certain applications, the proximal section 70 is at least about 10% and preferably at least about 20% longer than the distal section 72. For example, in one device adapted for the LAA closure application, the proximal section 70 in a six anchor device has a length of about 0.54 inches, and the distal section 72 has a length of about 0.40 inches. Each anchor support has an OD of about 0.045 inches. As with previous embodiments, the functional roles and/or the dimensions of the proximal and distal sections can be reversed and remain within the scope of the present invention. Optimization of the relative lever arm lengths can be determined for each application taking into account a variety of variables such as desired device diameter, target lumen or tissue aperture diameter, launch angle and desired pull forces for aiming and deployment.

The proximal end 71 of the proximal section 70 and distal end 73 of distal section 72 are movably secured to the closure catheter 38 in any of a variety of ways which will be apparent to those of skill in the art in view of the disclosure herein. In the illustrated embodiment, each anchor support 62 comprises a four segment component which may be constructed from a single length of tubing by providing an intermediate flex point 74, a proximal flex point 80 and a distal flex point 82. Distal flex point 82 provides a pivotable connection between the anchor support 62 and a distal connection segment 84. The distal connection segment 84 may be secured to the distal end of actuator 56 by any of a variety of techniques, such as soldering, adhesives, mechanical interfit or others, as will be apparent to those of skill in the art. In the illustrated embodiment, the distal connection segment 84 is secured to the distal end 66 of the actuator 56 by adhesive bonding.

The proximal flex point 80 in the illustrated embodiment separates the proximal section 70 from a proximal connection segment 86, which is attached to the catheter body 52. In this construction, proximal axial retraction of the actuator 56 with respect to the tubular body 52 will cause the distal connection segment 84 to advance proximally towards the proximal connection segment 86, thereby laterally displacing the flex point 74 away from the longitudinal axis of the closure catheter 38. As a consequence, each of the proximal section 70 and the distal section 72 are aimed at an angle which is inclined outwardly from the axis of the closure catheter 38.

In general, each flex point 80, 82 includes a hinge 81, 83 which may be, as illustrated, a strip of flexible material. The hinges 81 and 83 are preferably positioned on the inside radius of the flex points 80, 82, respectively, for many construction materials. For certain materials, such as Nitinol or other superelastic alloys, the hinges 81 and 83 can be positioned at approximately 90° or 180° or other angle around the circumference of the tubular anchor guide from the inside radius of the flex point.

A tissue anchor 90 is illustrated as positioned within the distal section 72, for deployment in a generally proximal direction. Alternatively, the anchor 90 can be loaded in the proximal section 70, for distal deployment. A variety of tissue anchors can be readily adapted for use with the closure catheter 38 of the present invention, as will be appreciated by those of skill in the art in view of the disclosure herein. In the illustrated embodiment, the tissue anchor 90 comprises a tubular structure having a body 92, and one or more barbs 94. Tubular body 92 is coaxially movably disposed about an introducer 96. Introducer 96 has a proximal section 98, and a sharpened distal tip 100 separated by an elongate distal section 102 for slideably receiving the tissue anchor 90 thereon.

The tissue anchor 90 in the illustrated embodiment comprises a tubular body 92 having an axial length of about 0.118 inches, an inside diameter of about 0.017 inches and an outside diameter of about 0.023 inches. Two or more barbs 94 may be provided by laser cutting a pattern in the wall of the tube, and bending each barb 94 such that it is biased radially outwardly as illustrated. The tissue anchor 90 may be made from any of a variety of biocompatible metals such as stainless steel, Nitinol, Elgiloy or others known in the art. Polymeric anchors such as HDPE, nylon, PTFE or others may alternatively be used. For embodiments which will rely upon a secondary closure structure such as staples, sutures or clips to retain the LAA or other cavity closed, the anchor may comprise a bioabsorbable or dissolvable material so that it disappears after a period of time. An anchor suture 108 is secured to the anchor.

In one embodiment of the invention, the introducer 96 has an axial length of about 0.250 inches. The proximal section 98 has an outside diameter of about 0.023 inches and an axial length of about 0.100 inches. The distal section 102 has an outside diameter of about 0.016 inches and an axial length of about 0.150 inches. The outside diameter mismatch between the proximal section 98 and the distal section 102 provides a distally facing abutment 104, for supporting the tubular body 92 of tissue anchor 90, during the tissue penetration step. A deployment wire (e.g., a suture) 106 is secured to the proximal end 98 of the introducer 96. The introducer 96 may be made in any of a variety of ways, such as extrusion or machining from stainless steel tube stock.

Figure 6A:
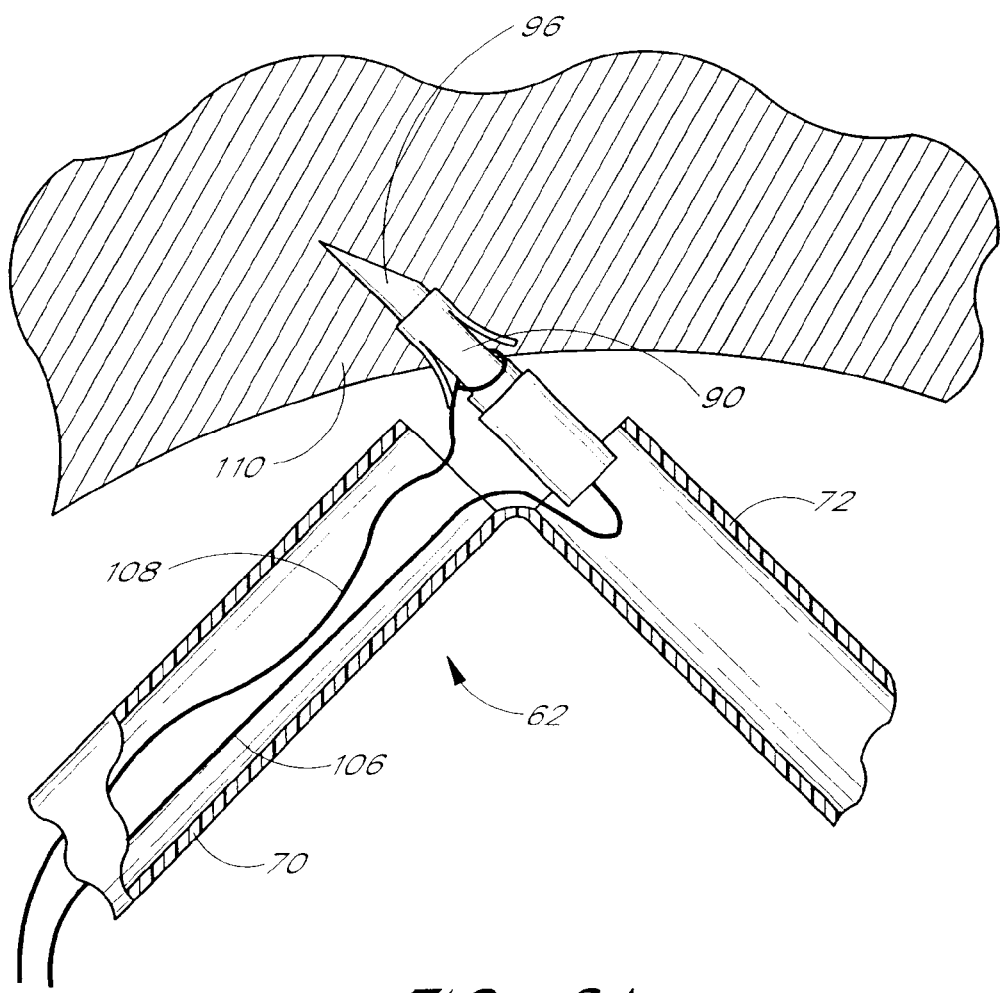
FIG. 6A is a schematic illustration of a tissue anchor and introducer advancing into a tissue surface.
Figure 6B:
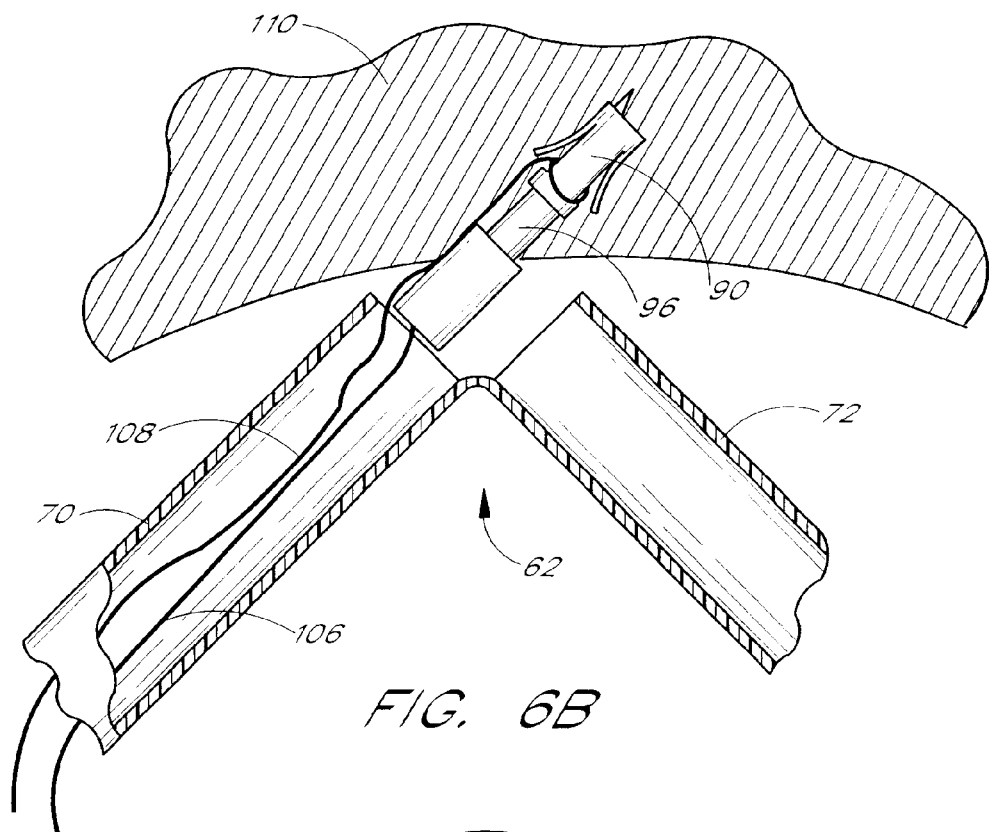
FIG. 6B is an illustration as in FIG. 6A, with the anchor positioned within the tissue and the introducer partially retracted.
Figure 6C:
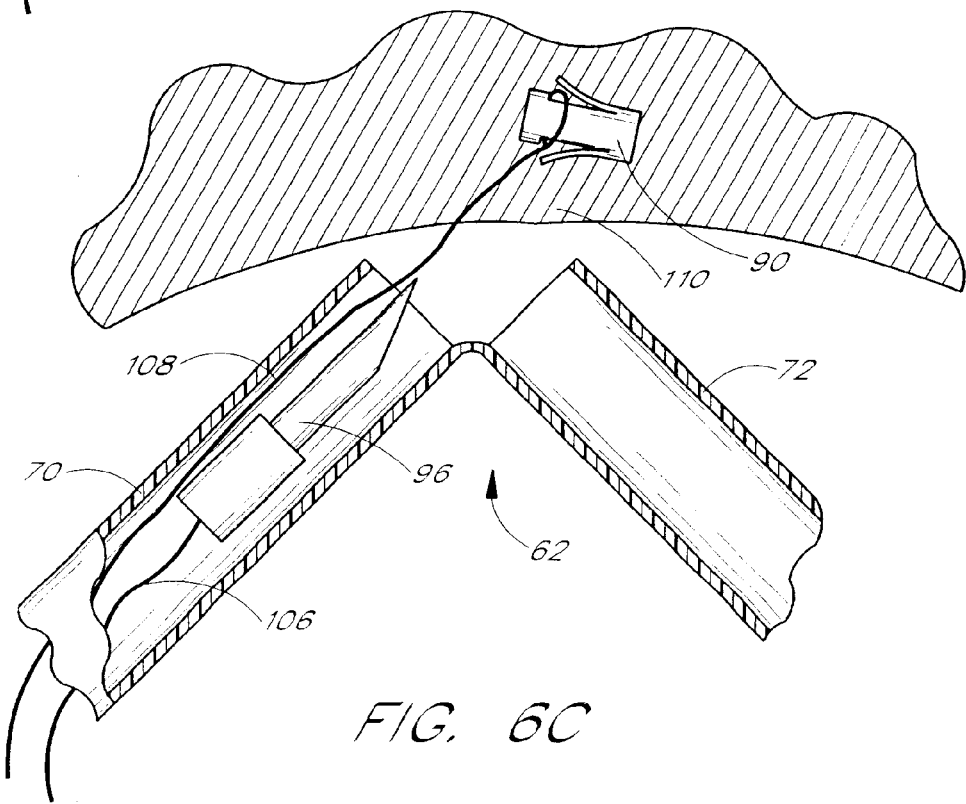
FIG. 6C is an illustration as in FIG. 6B, with the introducer fully retracted and the anchor positioned within the tissue.

Referring to FIGS. 6A–6C, introduction of the tissue anchor 90 into target tissue 110 is illustrated following inclination of the anchor support 62 with respect to the longitudinal axis of the closure catheter 38. Proximal retraction of the deployment wire 106 causes the tissue anchor 90 and introducer 96 assembly to travel axially through the distal section 72, and into the tissue 110. Continued axial traction on the deployment wire 106 causes the longitudinal axis of the introducer 96 to rotate, such that the introducer 96 becomes coaxially aligned with the longitudinal axis of the proximal section 70. Continued proximal traction on the deployment wire 106 retracts the introducer 96 from the tissue anchor 90, leaving the tissue anchor 90 in place within the tissue. The anchor suture 108 remains secured to the tissue anchor 90, as illustrated in FIG. 6C.

Figure 7:
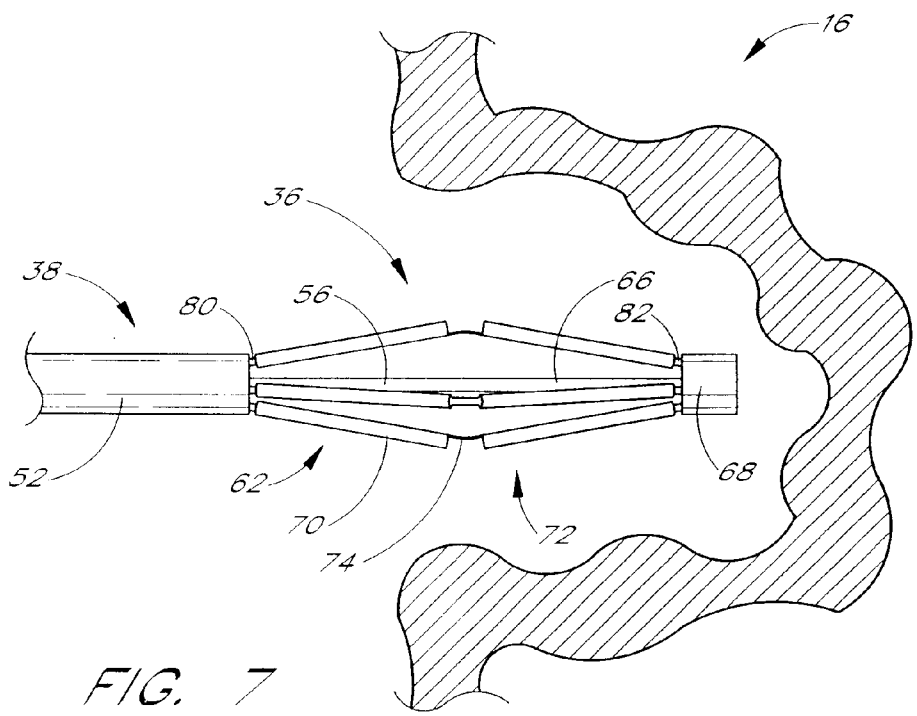
FIG. 7 shows a schematic view of a closure catheter disposed within the opening of the LAA.
Figure 8:
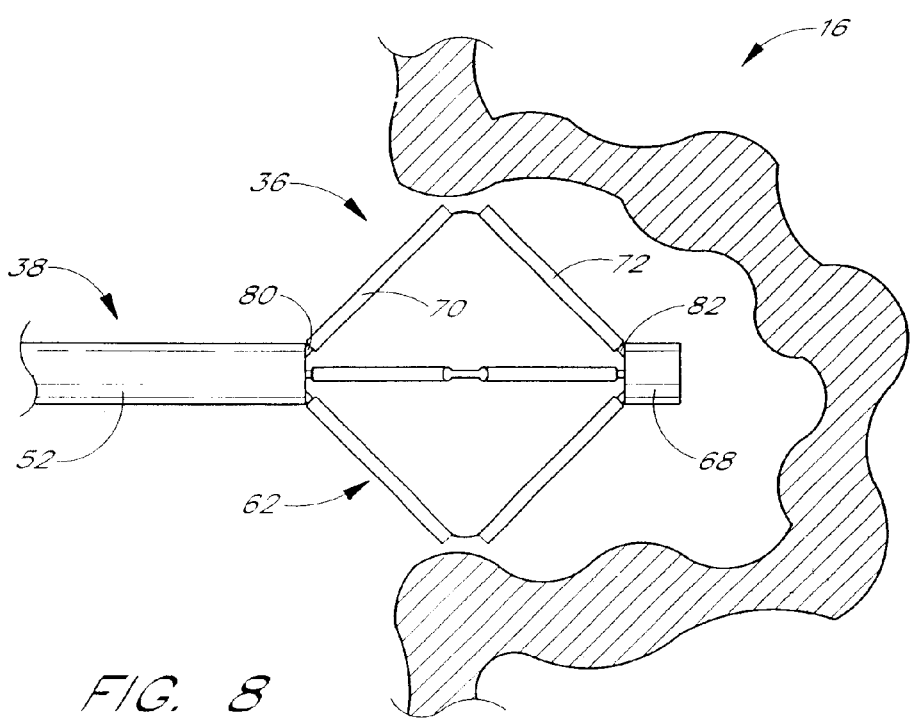
FIG. 8 is a schematic illustration of the opening of the LAA as in FIG. 7, with the anchor guides in an inclined orientation.

In use, the closure catheter 38 is percutaneously introduced into the vascular system and transluminally advanced into the heart and, subsequently, into the left atrial appendage using techniques which are known in the art. Referring to FIG. 7, the distal end 36 of the closure catheter 38 is positioned at about the opening of the LAA 16, and the position may be confirmed using fluoroscopy, echocardiography, or other imaging. The actuator 56 is thereafter proximally retracted, to incline the anchor supports 62 radially outwardly from the longitudinal axis of the closure catheter 38, as illustrated in FIG. 8. Preferably, the axial length of the proximal section 70 of each anchor support 62, in combination with the angular range of motion at the proximal flex point 80, permit the flex point 74 to be brought into contact with the tissue surrounding the opening to the LAA. In general, this is preferably accomplished with the distal section 72 inclined at an angle within a range of from about 45° to about 120° with respect to the longitudinal axis of the closure catheter 38. Actuator 56 may be proximally retracted until the supports 62 are fully inclined, or until tactile feedback reveals that the anchor supports 62 have come into contact with the surrounding tissue 110.

Figure 9:
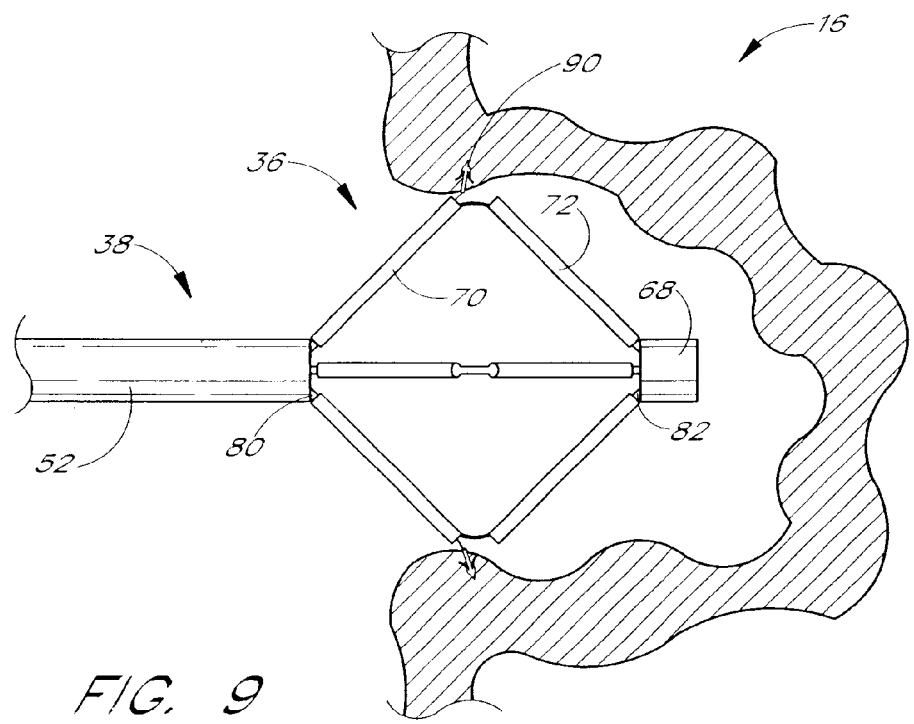
FIG. 9 is a schematic illustration as in FIG. 8, with tissue anchors deployed from the anchor guides.
Figure 10:
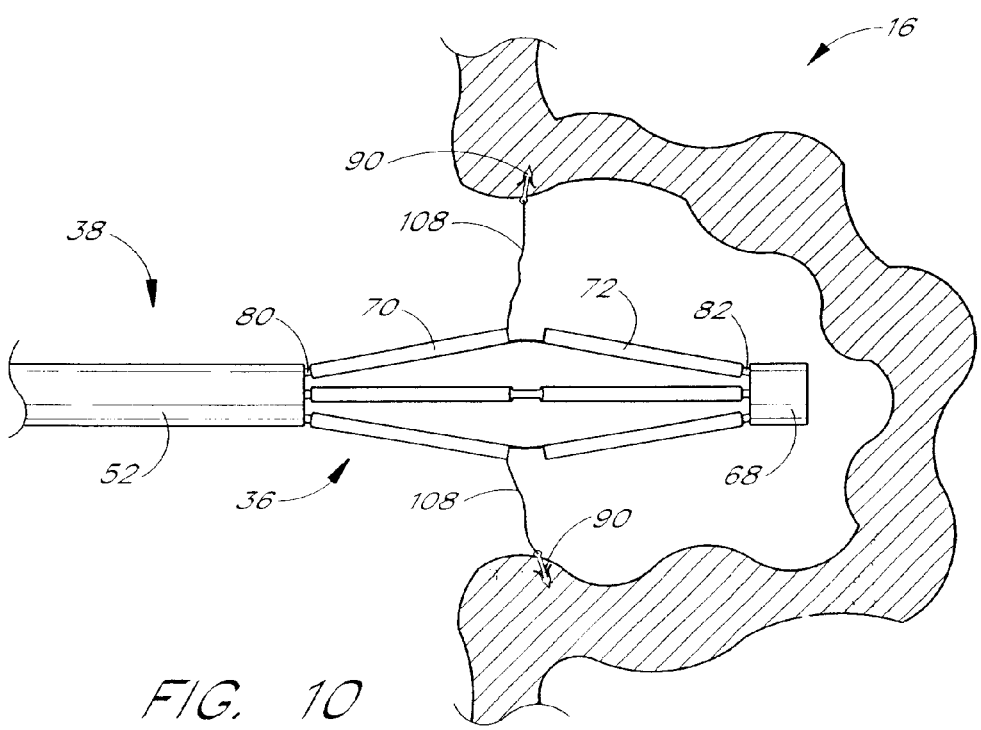
FIG. 10 is a schematic illustration as in FIG. 9, with the anchor guides retracted into an axial orientation.
Figure 11:
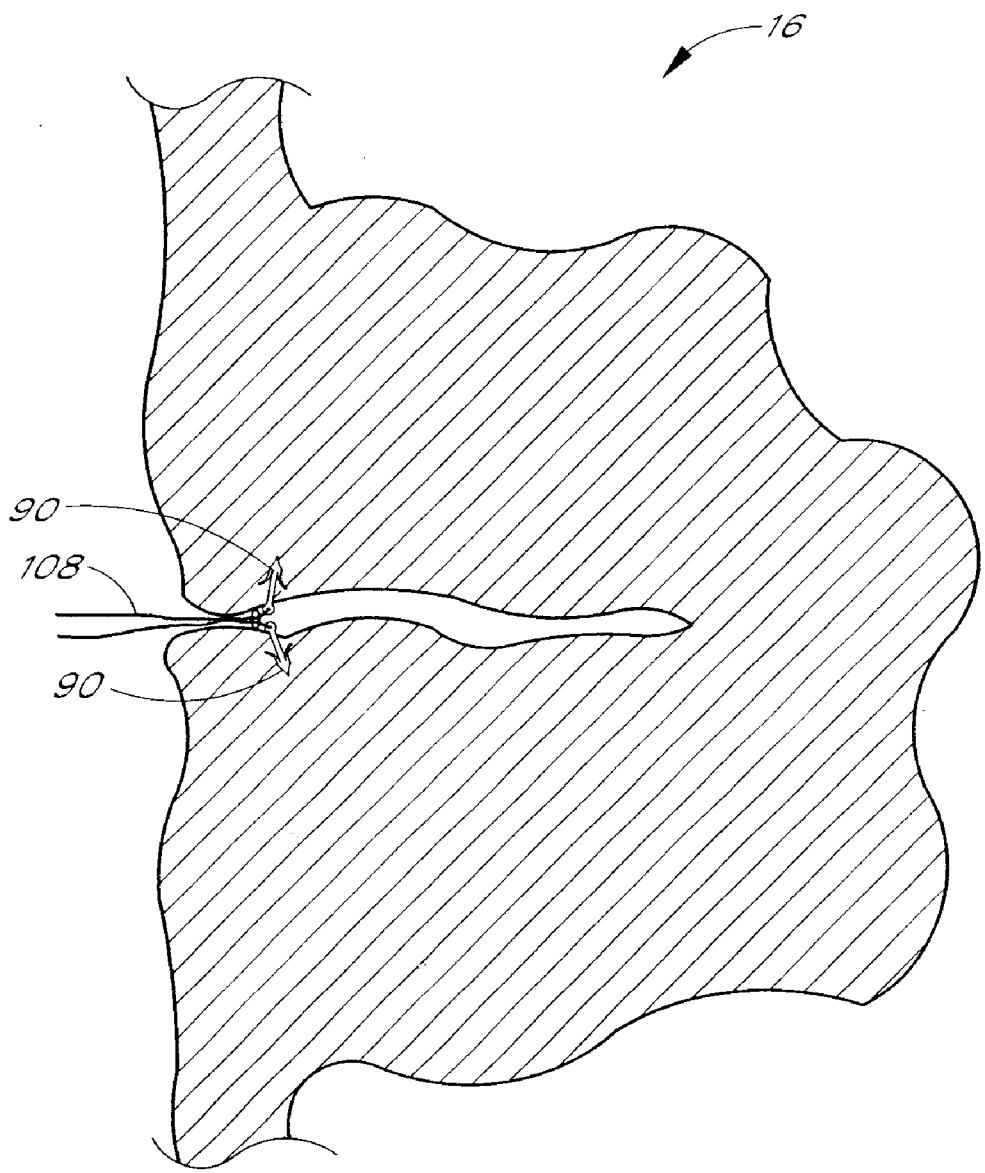
FIG. 11 is a schematic illustration as in FIG. 10, with the closure catheter retracted and the LAA drawn closed using the tissue anchors.

Following inclination of the anchor supports 62, the deployment wire 106 is proximally retracted thereby advancing each of the tissue anchors 90 into the surrounding tissue 110 as has been discussed. See FIG. 9. The anchor supports 62 are thereafter returned to the first, axial position, as illustrated in FIG. 10, for retraction from the left atrial appendage. Proximal retraction on the anchor sutures 108 such as through a tube, loop or aperture will then cause the left atrial appendage wall to collapse as illustrated in FIG. 11. Anchor sutures may thereafter be secured together using any of a variety of conventional means, such as clips, knots, adhesives, or others which will be understood by those of skill in the art. Alternatively, the LAA may be sutured, pinned, stapled or clipped shut, or retained using any of a variety of biocompatible adhesives.

In an alternate embodiment, a single suture is slideably connected to the at least three and preferably five or more anchors such that proximal retraction of the suture following deployment of the anchors draws the tissue closed in a "purse string" fashion. A similar technique is illustrated in FIGS. 31A and 31B in U.S. Pat. No. 5,865,791 to Whayne, et al., the disclosure of which is incorporated in its entirety herein by reference.

The foregoing closure techniques may be accomplished through the closure catheter, or through the use of a separate catheter. The closure catheter may thereafter be proximally retracted from the patient, and the percutaneous and vascular access sites closed in accordance with conventional puncture closure techniques.

In accordance with a further aspect of the present invention, the closure catheter 38 with modifications identified below and/or apparent to those of skill in the art in view of the intended application, may be utilized to close any of a variety of tissue apertures. These include, for example, atrial septal defects, ventricle septal defects, patent ductus arteriosis, patent foreman ovale, and others which will be apparent to those of skill in the art. Tissue aperture closure techniques will be discussed in general in connection with FIGS. 12–17.

Figure 12:
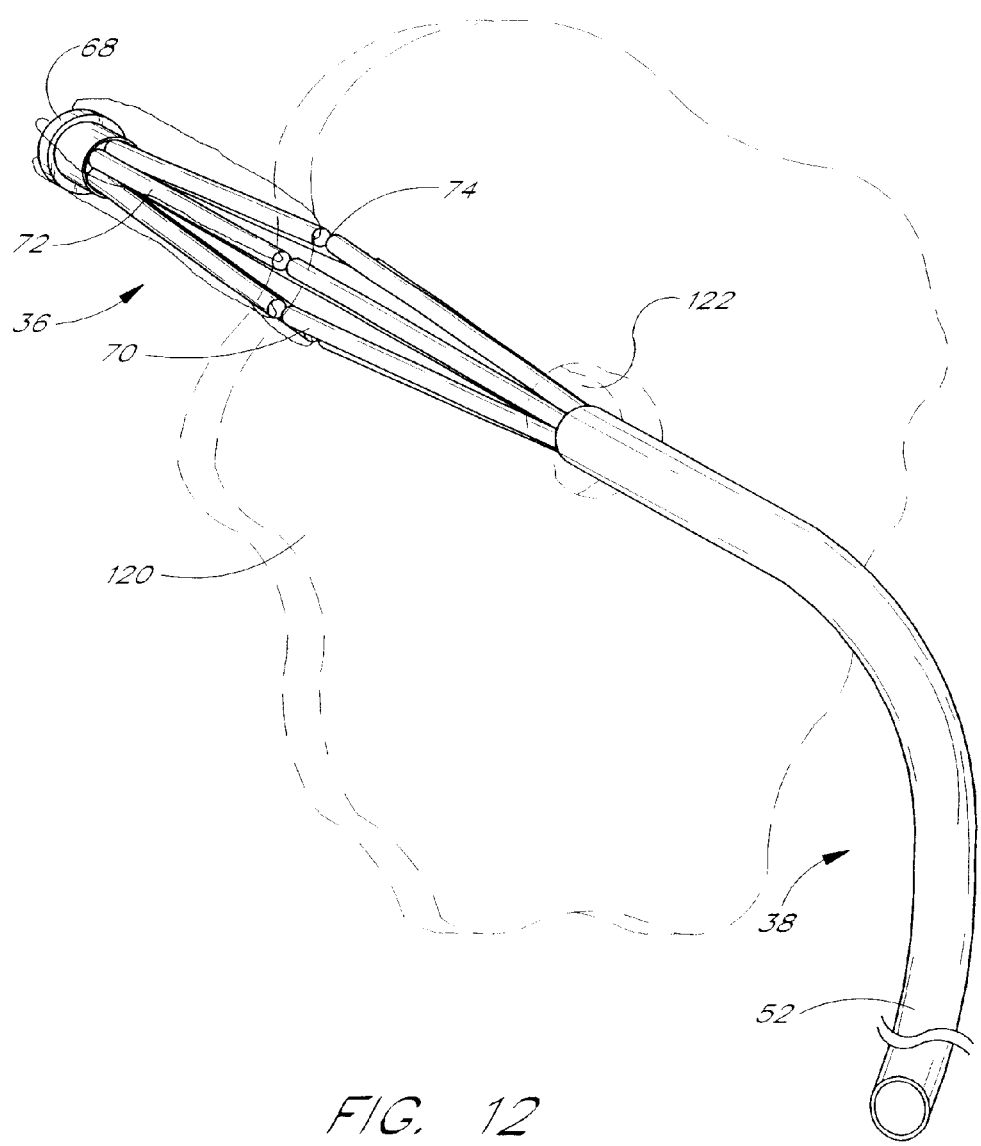
FIG. 12 is a perspective view of a closure catheter in accordance with the present invention positioned within a tissue aperture, such as an atrial septal defect.

Referring to FIG. 12, there is schematically illustrated a fragmentary view of a tissue plane 120 such as a septum or other wall of the heart. Tissue plane 120 contains an aperture 122, which is desirably closed. The closure catheter 38 is illustrated such that at least a portion of the distal end 36 extends through the aperture 122. Although the present aspect of the invention will be described in terms of a retrograde or proximal tissue anchor advancement from the back side of the tissue plane, the anchor deployment direction can readily be reversed by one of ordinary skill in the art in view of the disclosure herein, and the modifications to the associated method would be apparent in the context of a distal anchor advancement embodiment. In general, the proximal anchor advancement method, as illustrated, may desirably assist in centering of the catheter within the aperture, as well as permitting positive traction to be in the same direction as anchor deployment.

Closure catheter 38 is provided with a plurality of anchor supports 62 as have been described previously herein. In an embodiment intended for atrial septal defect closure, anywhere within the range of from about 3 to about 12 anchor supports 62 may be utilized.

Referring to FIG. 13, each anchor support 62 comprises a proximal section 70, a distal section 72, and a hinge or flex point 74 therebetween as has been previously discussed. At least one anchor 90 is carried by each anchor support 62, such as within the tubular distal section 72 in the context of a proximal deployment direction embodiment. Anchor 90 is connected to an anchor suture 108 as has been discussed. In the illustrated embodiment, the anchor suture 108 extends along the outside of the anchor support 62 and into the distal opening of a lumen in tubular body 52. The anchor sutures 108 may, at some point, be joined into a single element, or distinct anchor sutures 108 may extend throughout the length of the catheter body to the proximal end thereof.

As shown in FIG. 13, the anchor support 62 is advanced from a generally axially extending orientation to an inclined orientation to facilitate deployment of the anchor 90 into the tissue plane 120 adjacent aperture 122. Preferably, the geometry of the triangle defined by distal section 72, proximal section 70 and the longitudinal axis of the catheter is selected such that the plurality of anchors 90 will define a roughly circular pattern which has a greater diameter than the diameter of aperture 122. Thus, the length of proximal section 70 will generally be greater than the approximate radius of the aperture 122.

In general, for atrial septal defect applications, the circle which best fits the anchor deployment pattern when the distal section 72 is inclined to its operative angle will have a diameter within the range of from about 0.5 centimeters to about 3 centimeters. Dimensions beyond either end of the foregoing range may be desirable to correct defects of unusual proportions. In addition, it is not necessary that the anchors define a circular pattern when deployed into the tissue plane 120. Non-circular patterns such as polygonal, elliptical, oval or other, may be desirable, depending upon the nature of the aperture 122 to be closed.

FIG. 13 illustrates the anchors 90 partially deployed into or through the tissue plane 120. In general, the anchors 90 may either be designed to reside within the tissue plane 120 such as for locations of the aperture 120 which are adjacent relatively thick tissues. Alternatively, the tissue anchor 90 may be designed to reside on one side of the tissue plane 120, and attached to a suture which extends through the tissue plane 120 as illustrated in FIGS. 14 and 15.

Referring to FIG. 14, the closure catheter 38 is illustrated as returned to the generally axial orientation and proximally retracted through the aperture 122 following deployment of a plurality of tissue anchors 90. The anchor sutures 108 may thereafter be proximally retracted from the proximal end of the closure catheter 38, thereby drawing the tissue surrounding aperture 122 together to close the aperture. The anchor sutures 108 may thereafter be secured together in any of a variety of manners, such as by clamping, knotting, adhesives, thermal bonding or the like.

In the illustrated embodiment, the closure catheter 38 carries a detachable clamp 124 which may be deployed from the distal end of the closure catheter 38 such as by a push wire, to retain the anchor sutures 108. The clamp 124 may be an annular structure with an aperture therein for receiving the anchor sutures 108. The clamp is carried on the catheter in an "open" position and biased towards a "closed" position in which it tightens around the sutures 108. A ring of elastomeric polymer or a shape memory metal alloy may be used for this purpose. Any of a variety of clamps, clips, adhesives, or other structures may be utilized to secure the anchor sutures 108 as will be appreciated by those of skill in the art in view of the disclosure herein. Anchor sutures 108 may thereafter be severed such as by mechanical or thermal means, and the closure catheter 38 is thereafter retracted from the treatment site.

In accordance with a further aspect of the present invention, the closure catheter 38 is provided with a deployable patch 126, as illustrated in FIGS. 16 and 17. The patch 126 may comprise of any of a variety of materials, such as PTFE, Dacron, or others depending upon the intended use. Suitable fabrics are well-known in the medical device art, such as those used to cover endovascular grafts or other prosthetic devices.

The patch 126 is preferably carried by the distal sections 72 of the anchor support 62. In the illustrated embodiment, the tissue anchors 90 are carried within the proximal section 70 of anchor support 62. In this manner, as illustrated in FIG. 17, the patch 126 is automatically unfolded and positioned across the aperture 122 as the anchor supports 62 are inclined into the anchor deployment orientation. The tissue anchor 90 may thereafter be advanced through the patch 126 and into the tissue plane 120 to tack the patch 126 against the opening 122. Alternatively, the tissue anchors may be deployed in a pattern which surrounds but does not penetrate the tissue patch. In this embodiment, the tissue anchors are preferably connected to the tissue patch such as by a suture. The tissue anchors may also both be connected to the patch or to each other by sutures and penetrated through the patch into the target tissue.

Tissue anchors 90 may be deployed proximally by pulling the deployment wire 106. Alternatively, tissue anchors 90 with or without an anchor suture 108, may be deployed from the proximal section 70 by a push wire axially movably positioned within the proximal section 70. Tissue anchors 90 may be carried on an introducer 96 as has been discussed previously herein.

The patch 126 may be retained on the distal section 72 in any of a variety of ways, such as through the use of low strength adhesive compositions, or by piercing the anchors 90 through the material of the patch 126 during the catheter assembly process.

Figures 18, 19, 20:
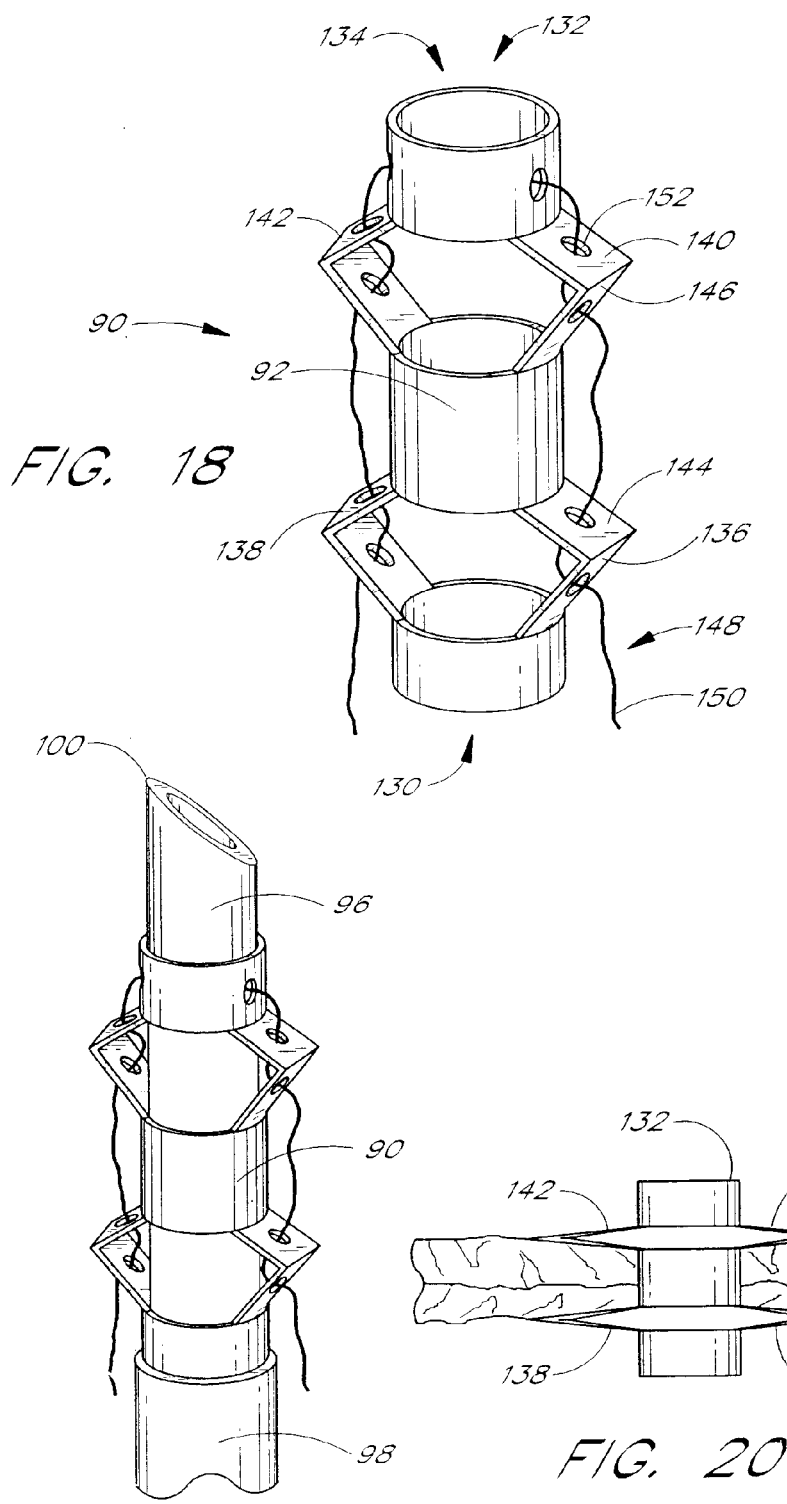
FIG. 18 is a perspective view of a buckling rivet type anchor in accordance with the present invention.
FIG. 19 is a perspective view of the buckling rivet of FIG. 18, carried by an introducer.
FIG. 20 is a cross-sectional schematic view of a buckling rivet of the type shown in FIG. 18, deployed on a tissue membrane.

Referring to FIGS. 18 through 20, there is disclosed an alternate anchor 90 in accordance with the present invention.

The anchor 90 may be utilized to anchor a suture within a solid tissue mass, or, as illustrated in FIG. 20, to secure a graft or patch to a tissue plane.

Referring to FIG. 18, anchor 90 comprises a proximal end 130, a distal end 132 and a central lumen 134 extending therebetween. Central lumen 134 allows the anchor 90 to be positioned on an introducer 96 as is illustrated in FIG. 19, and has been previously discussed.

The anchor 90 is provided with at a least first proximal projection 136 and a second proximal projection 138. First and second proximal projections 136 and 138 are designed to enlarge radially outwardly in response to axial compression of the anchor 90. Thus, in an uncompressed configuration such as that illustrated in FIG. 19, the first and second proximal projections 136 and 138 extend generally in parallel with the longitudinal axis of the anchor 90. A distally facing tissue contact surface 144 is forced to incline radially outwardly in response to axial shortening of the anchor 90, as will be apparent to those of skill in the art in view of the illustration in FIG. 18. Although illustrated with two proximal projections positioned at approximately 180° apart from each other, three or four or more proximal projections may be provided, preferably evenly distributed about the circumference of the anchor 90.

At least a first distal projection 140, and preferably a second distal projection 142 are provided on the tubular body 92 spaced distally apart from the proximal projections. First and second distal projections 140 and 142 similarly expand or enlarge radially outwardly in response to axial compression of the anchor 90. Axial separation between the first proximal projection 136 and first distal projection 140 allows the anchor 90 to secure a patch 126 or graft or other structure to a tissue plane 120 as illustrated in FIG. 20, by sandwiching the patch 126 and tissue plane 120 between distally facing tissue contact surface 144 and proximally facing tissue contact surface 146. The anchor 90 can be deployed from the introducer 96, utilizing any of the deployment catheters disclosed elsewhere herein.

The radial enlargement of the proximal and distal projections is accomplished by axially shortening the anchor 90 along its longitudinal axis. This may be accomplished by preventing proximal movement of proximal end 130 by seating the proximal end 130 against the proximal section 98 of an introducer 96, such as illustrated in FIG. 19. The distal end 132 is thereafter advanced proximally, such as by proximal traction on a proximal force transmitter 148 which may be a suture 150. Suture 150 may extend in a loop through a plurality of apertures 152, extending through the proximal and distal projections. Alternatively, the suture 150 may extend alongside the anchor 90 or through central lumen 134 depending upon the tolerance between the central lumen 134 and the introducer 96. Alternative proximal force transmitter structures may also be utilized, as will be apparent to those of skill in the art.

The anchor 90 may be manufactured in a variety of ways, such as by cutting or etching from a metal or polymeric tube. Preferably, the anchor 90 is laser cut from a Nitinol or steel tube having an outside diameter within the range of from about 0.014" to about 0.038" and an axial length within the range of from about 0.050" to about 0.250. The axial length of each of the distally facing tissue contact surface 144 and proximally facing tissue contact 146 is within the range of from about 0.010" to about 0.060". The wall thickness of the tube is within the range of from about 0.002" to about 0.012". Full axial compression of most metal tube embodiments will bend the metal beyond its elastic limit at each apex on the various projections, such that the suture 150 may be removed from the anchor 190 following deployment and the anchor will remain in its deployed (axially compressed) configuration as illustrated in FIG. 20.

Although illustrated primarily as an embodiment intended for attaching a patch or other membrane to a tissue plane, the anchor 90 illustrated in FIG. 18 may also be used to anchor a suture to a solid tissue mass as discussed previously herein. For this purpose, the anchor may be simplified to include only a first and second proximal projection 136 and 138, or additional projections in the same plane as the first and second proximal projections. However, first and second distal projections or additional projections may be added, depending upon the desired pull force required to dislodge the anchor 90 from the implanted position within the tissue.

The cardiac defects may be accessed via catheter through a variety of pathways. An ASD or VSD may be accessed from the arterial circuit. The catheter is introduced into the arterial vascular system and guided up the descending thoracic and/or abdominal aorta. The catheter may then be advanced into the left ventricle (LV) through the aortic outflow tract. Once in the LV, the patch may be deployed in the VSD. Alternatively, once in the LV, the patch may be directed up through the mitral valve and into the left atrium (LA). When the patch is in the LA, it may be directed into the ASD and installed.

Alternatively, an ASD or VSD may be accessed from the venous circuit. The catheter with a patch thereon may be introduced into the venous system, advanced into the Inferior Vena Cava (IVC) or Superior Vena Cava (SVC) and guided into the right atrium (RA). The patch may then be directed into the ASD. Alternatively, once in the RA, the patch may be advanced through the tricuspid valve and into the right ventricle (RV) and directed into the VSD and installed.

Referring to FIGS. 21A–21G, there are illustrated a variety of tissue anchors which may be used in the tissue closure or attachment device of the present invention. Each of FIGS. 21A and 21B disclose an anchor having a body 92, a distal tip 101, and one or more barbs 94 to resist proximal movement of the anchor. An aperture 107 is provided to receive the anchor suture. The embodiments of FIGS. 21A and 21B can be readily manufactured such as by stamping or cutting out of flat sheet stock.

Figure 21A:
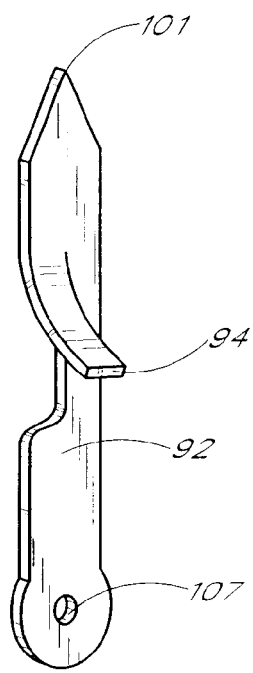
FIGS. 21A–21G are alternate tissue anchors for use with the closure catheter of the present invention.
Figure 21B:
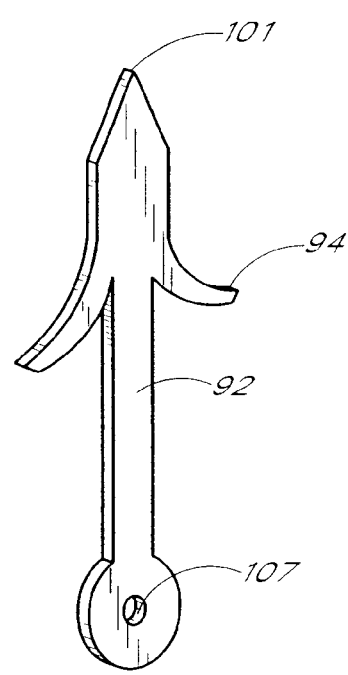
Figure 21C:
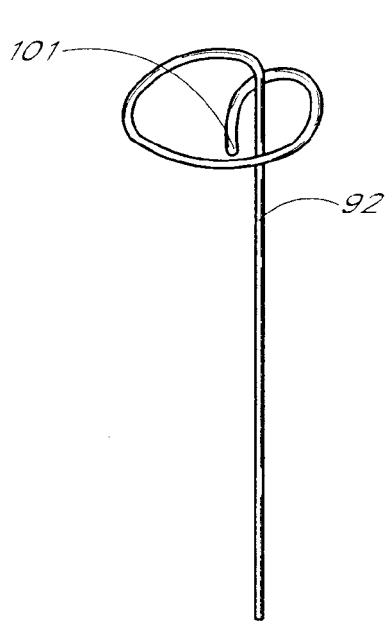

The anchor illustrated in FIG. 21C comprises a wire having a body 92 and a distal tip 101. The wire preferably comprises a super-elastic alloy such as Nitinol or other nickel titanium-based alloy. The anchor is carried within a tubular introducer, in a straight orientation, for introduction into the tissue where the anchor is to reside. As the body 92 is advanced distally from the carrier tube, the anchor resumes its looped distal end configuration within the tissue, to resist proximal retraction on the wire body 92.

Figure 21D:
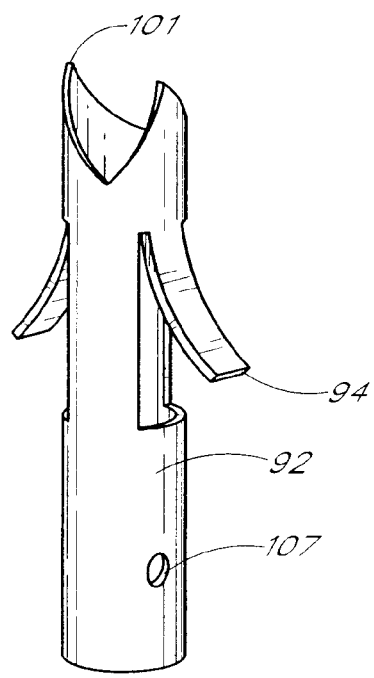

FIG. 21D illustrates a tubular anchor, which may be manufactured from a section of hypotube, or in the form of a flat sheet which is thereafter rolled about a mandrel and soldered or otherwise secured. The anchor comprises a distal tip 101, one or more barbs 94, and an aperture 107 for securing the anchor suture. The anchor of FIG. 21D may be carried by and deployed from the interior of a tubular anchor support as has been discussed. Alternatively, the anchor of FIG. 21D can be coaxially positioned over a central tubular or solid anchor support wire.

Figures 21E, 21F:
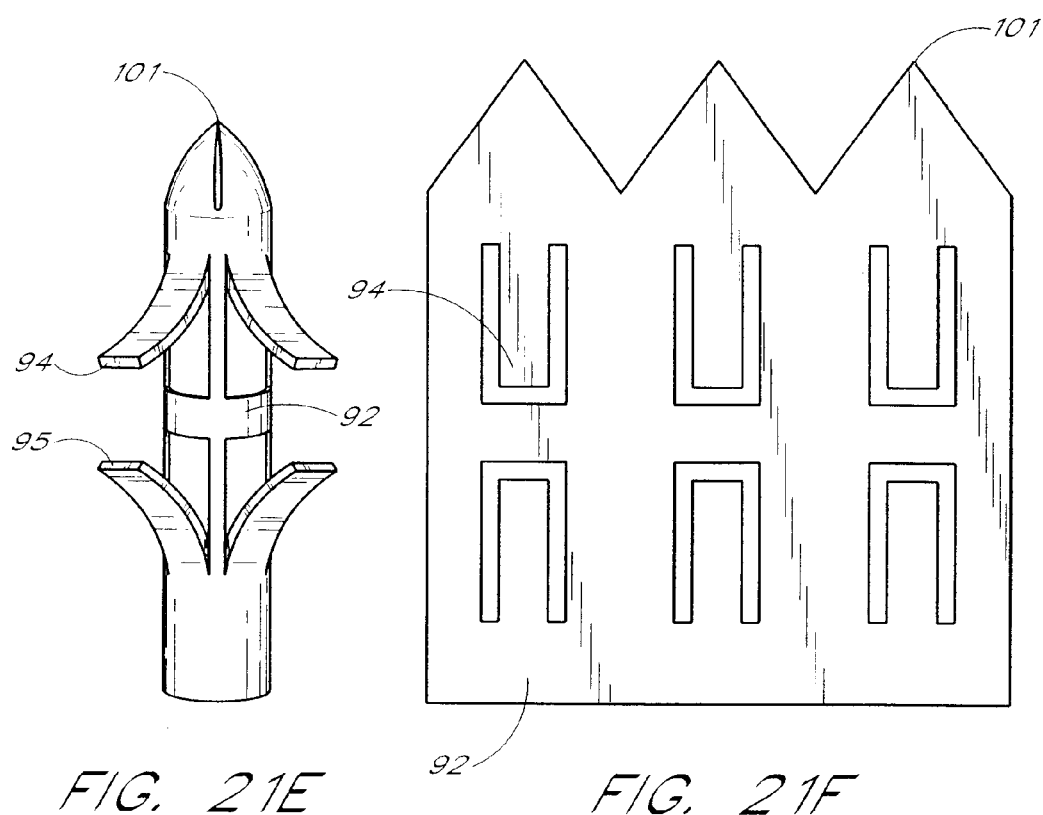
Figure 21G:
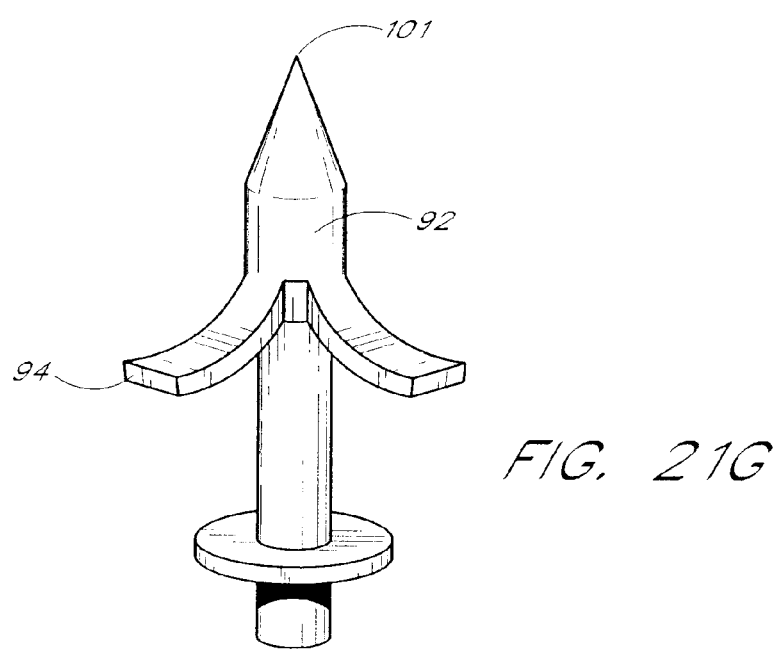

FIG. 21E illustrates an anchor which may be formed either by cutting from tube stock or by cutting a flat sheet such as illustrated in FIG. 21F which is thereafter rolled about an axis and soldered or otherwise secured into a tubular body. In this embodiment, three distal tips 101 in the flat sheet stock may be formed into a single distal tip 101 in the finished anchor as illustrated in FIG. 21E. One or more barbs 94 may be formed by slotting the sheet in a U or V-shaped configuration as illustrated. The anchor in FIG. 21E is additionally provided with one or more barbs 95 which resist distal migration of the anchor. This may be desirable where the anchor is implanted across a thin membrane, or in other applications where distal as well as proximal migration is desirably minimized.

Although the present invention has been described in terms of certain preferred embodiments, other embodiments will become apparent to those of skill in the art in view of the disclosure herein. Accordingly, the scope of the invention is not intended to be limited by the specific disclosed embodiments, but, rather, by the attached claims.

What is claimed is:

1. A method of patching an atrial septal defect, comprising the steps of:
   providing a catheter having an elongate, flexible body with a proximal end and a distal end, a patch and at least two anchors removably carried by the distal end;
   advancing the distal end to a position near the atrial septal defect;
   positioning the patch across the defect; and
   deploying the anchors from the catheter to secure the patch across the defect.

2. A method of patching an atrial septal defect as in claim 1, wherein the positioning step comprises enlarging the cross section of the patch from a reduced profile for advancing the catheter to an enlarged profile for patching the defect.

3. A method of patching an atrial septal defect as in claim 1, wherein the positioning step comprises inclining at least one patch support from an axial orientation to an inclined orientation to position the patch across the defect.

4. A method of patching an atrial septal defect as in claim 3, wherein the positioning step comprises inclining at least three patch supports from an axial orientation to an inclined orientation to position the patch across the defect.

5. A method of patching an atrial septal defect as in claim 3, wherein the deploying the anchors step comprises advancing the anchors distally through the patch and into tissue adjacent the defect to secure the patch across the defect.

6. A method of closing an opening in a subcutaneous tissue plane, comprising the steps of:
   providing a catheter having a longitudinal axis, a patch and at least one anchor thereon;
   advancing the catheter to the opening;
   positioning the patch across the opening such that the patch is approximately parallel to the tissue plane and transverse to the longitudinal axis; and
   advancing the anchor into tissue to secure the patch across the opening.

7. A method of closing an opening in a subcutaneous tissue plane as in claim 6, wherein the advancing the anchor step comprises advancing the anchor through the patch and into the tissue.

8. A method of closing an opening in a subcutaneous tissue plane as in claim 6, wherein the advancing the anchor step comprises advancing at least three anchors into the tissue to secure the patch across the opening.

9. A method of closing an opening in a subcutaneous tissue plane as in claim 6, wherein the opening is a naturally occurring opening.

10. A method of closing an opening in a subcutaneous tissue plane as in claim 9, wherein the opening is an atrial septal defect.

11. A method of closing an opening in a subcutaneous tissue plane as in claim 6, wherein the opening is a surgically created opening.

12. A method of closing an opening in a subcutaneous tissue plane as in claim 6, further comprising the step of unfolding the patch from a reduced configuration to an enlarged configuration prior to the advancing the anchor step.

13. A deployment catheter for deploying a patch across a tissue aperture, comprising:
   an elongate body, having a proximal end and a distal end;
   at least one patch support for removably carrying a patch; and
   at least one anchor support hingeably connected to the patch support for removably carrying at least one anchor.

14. A deployment catheter as in claim 13, wherein the anchor support is movable between an axial orientation and an inclined orientation with respect to a longitudinal axis of the body.

15. A deployment catheter as in claim 14, wherein the anchor support is hingably connected to the patch support.

16. A deployment catheter as in claim 15, comprising at least four anchor supports and at least four patch supports.

17. A deployment catheter as in claim 14, further comprising a control on the proximal end of the body, wherein the anchor support is movable from the axial orientation to the inclined orientation in response to manipulation of the control.

18. A patch deployment catheter for deploying a patch across an opening, comprising:
   an elongate body, having a proximal end and a distal end;
   at least two supports on the catheter, movable between an axial orientation and an inclined orientation, each support comprising a proximal section, a distal section, and a hinge in between; and
   a control on the catheter for moving the hinge radially outwardly from a first position for introducing the catheter to a site in the body to a second position for deploying the patch at the site;
   wherein the supports are in the axial orientation when the hinge is in the first position.

19. A patch deployment catheter as in claim 18, wherein the body is flexible.

20. A patch deployment catheter as in claim 18, further comprising at least one tissue anchor carried by the proximal section of each support.

21. A patch deployment catheter as in claim 18, further comprising at least one patch carried by the distal section of each support.

22. A patch deployment catheter as in claim 21, comprising a tissue ingrowth surface on the patch.

23. A patch deployment catheter as in claim 20, wherein the proximal section comprises a tube and the tissue anchor is removably carried inside of the tube.

24. A patch deployment catheter as in claim 23, further comprising a deployment actuator extending throughout the length of the catheter, and the tissue anchor is advanced distally out of tube in response to axial movement of the actuator.

* * * * *